(12) United States Patent
Wang et al.

(10) Patent No.: US 10,653,321 B2
(45) Date of Patent: May 19, 2020

(54) PHOTOACOUSTIC COMPUTED TOMOGRAPHY WITH A BIPLANAR ACOUSTIC REFLECTOR

(71) Applicant: Washington University, St. Louis, MO (US)

(72) Inventors: Lihong Wang, St. Louis, MO (US); Bin Huang, St. Louis, MO (US); Jun Xia, St. Louis, MO (US); Konstantin Maslov, St. Louis, MO (US); Mark Anastasio, St. Louis, MO (US)

(73) Assignee: Washington University, St. Louis, MO (US)

( * ) Notice: Subject to any disclaimer, the term of this patent is extended or adjusted under 35 U.S.C. 154(b) by 528 days.

(21) Appl. No.: 15/036,303

(22) PCT Filed: Nov. 12, 2014

(86) PCT No.: PCT/US2014/065195
§ 371 (c)(1),
(2) Date: May 12, 2016

(87) PCT Pub. No.: WO2015/073523
PCT Pub. Date: May 21, 2015

(65) Prior Publication Data
US 2016/0262628 A1  Sep. 15, 2016
US 2017/0367586 A9  Dec. 28, 2017

Related U.S. Application Data

(60) Provisional application No. 61/902,918, filed on Nov. 12, 2013.

(51) Int. Cl.
*A61B 5/00* (2006.01)
*A61B 8/00* (2006.01)

(52) U.S. Cl.
CPC .......... *A61B 5/0095* (2013.01); *A61B 8/4245* (2013.01); *A61B 8/4483* (2013.01); *A61B 2503/40* (2013.01)

(58) Field of Classification Search
CPC .................................... A61B 5/0095
See application file for complete search history.

(56) References Cited

U.S. PATENT DOCUMENTS 4,495,817 A   1/1985  Hunt et al.
5,577,506 A * 11/1996  Dias ................ A61B 8/12
                                              310/366

(Continued)

FOREIGN PATENT DOCUMENTS

WO       2013099139 A1     7/2013

OTHER PUBLICATIONS

Cox, B. T., Arridge, S. R., & Beard, P. C. (2007). Photoacoustic tomography with a limited-aperture planar sensor and a reverberant cavity. Inverse Problems, 23(6), S95. (Year: 2007).*

(Continued)

*Primary Examiner* — Theodore J Stigell
*Assistant Examiner* — Johnathan Maynard
(74) *Attorney, Agent, or Firm* — Armstrong Teasdale LLP

(57) ABSTRACT

Systems and methods for improving limited-view photoacoustic tomography using an acoustic reflector are described. In particular, an acoustic reflector and ultrasonic transducer array are integrated to provide a virtual array that enhances the field of view of the ultrasonic transducer array, thereby improving the quality of photoacoustic tomography images obtained using the systems and methods described herein.

19 Claims, 9 Drawing Sheets

(56) References Cited

U.S. PATENT DOCUMENTS

| | | | |
|---|---|---|---|
| 6,543,272 B1 | 4/2003 | Vitek | |
| 8,353,833 B2 | 1/2013 | Dogra et al. | |
| 2006/0058664 A1 | 3/2006 | Barthe et al. | |
| 2006/0058678 A1* | 3/2006 | Vitek | A61B 8/4281 600/459 |
| 2008/0275344 A1* | 11/2008 | Glide-Hurst | A61B 8/0825 600/442 |
| 2011/0021924 A1 | 1/2011 | Sethuraman et al. | |
| 2011/0275890 A1* | 11/2011 | Wang | A61B 5/0062 600/104 |
| 2012/0204648 A1* | 8/2012 | Wang | A61B 5/0095 73/606 |
| 2012/0220851 A1* | 8/2012 | Razansky | A61B 5/0073 600/407 |
| 2012/0275262 A1* | 11/2012 | Song | G01N 29/0654 367/7 |
| 2013/0041260 A1* | 2/2013 | Schmidt | A61B 8/0825 600/442 |

OTHER PUBLICATIONS

Wu, D., Wang, X., Tao, C., & Liu, X. J. (2011). Limited-view photoacoustic tomography utilizing backscatterers as virtual transducers. Applied Physics Letters, 99(24), 244102. (Year: 2011).*
Xia, J., Chatni, M. R., Maslov, K. I., Guo, Z., Wang, K., Anastasio, M. A., & Wang, L. V. (2012). Whole-body ring-shaped confocal photoacoustic computed tomography of small animals in vivo. Journal of biomedical optics, 17(5), 050506. (Year: 2012).*
Hu, S., & Wang, L. V. (2010). Photoacoustic imaging and characterization of the microvasculature. Journal of biomedical optics, 15(1), 011101. (Year: 2010).*
Montilla, L. G., Olafsson, R., & Witte, R. S. (2010). Real-time pulse echo and photoacoustic imaging using an ultrasound array and in-line reflective illumination. In Photons Plus Ultrasound: Imaging and Sensing 2010 (vol. 7564, p. 75643C). International Society for Optics and Photonics. (Year: 2010).*
International Search Report issued for PCT/US2014/065195 dated Feb. 23, 2015 (2 pages).
Written Opinion issued for PCT/US2014/065195 dated Feb. 23, 2015 (6 pages).
Anastasio, M. A. et al., "Half-Time Image Reconstruction in Thermoacoustic Tomography," IEEE Transactions on Medical Imaging, 24(2): 199-210 (2005).
Angelsen, B. A.J. et al., "Which Transducer Array is Best?" European Journal of Ultrasound, 2(2): 151-164 (1995).
Bassett, L. W. et al., "Breast Sonography" American Journal of Roentgenology, 156: 449-455 (1991).
Brecht, H-P. et al. "Whole-Body Three-Dimensional Optoacoustic Tomography System for Small Animals," Journal of Biomedical Optics, 14(6): 064007-064008 (2009).
Brenner, D. J. et al., "Computed Tomography—An Increasing Source of Radiation Exposure," The New England Journal of Medicine, 357(22): 2277-2284 (2007).
Buehler, A. et all, "Video Rate Optoacoustic Tomography of Mouse Kidney Perfusion," Optics Letters, 35(14): 2475-2477 (2010).
Choe, R et al., "Diffuse Optical Tomography of Breast Cancer During Neoadjuvant Chemotherapy: A Case Study with Comparison to MRI," Medical Physics, 32(4): 1128-1139 (2005).
Cox, B. T., et al. "Photoacoustic Tomography with a Limited-Aperture Planar Sensor and a Reverberant Cavity," Inverse Problems, 23(6): S95-S112 (2007).
Ermilov, S. A. et al., "Development of Laser Optoacoustic and Ultrasonic Imaging System for Breast Cancer Utilizing Handheld Array Probes," Proceedings of SPIE, 7177: 717703 (2009).
Ermilov, S. A. et al., "Laser Optoacoustic Imaging System for Detection of Breast Cancer," Journal of Biomedical Optics, 14(2): 024007 (2009).
Fang, H. et al., "Photoacoustic Doppler Effect from Flowing Small Light-Absorbing Particles," Physical Review Letters, 99(18): 184501 (2007).
Filonov, G. S. et al., "Deep-Tissue Photoacoustic Tomography of a Genetically Encoded Near-Infrared Fluorescent Probe," Angewandte Chemie International Edition, 51(6): 1448-1451 (2012).
Gamelin, J. et al. "A Real-Time Photoacoustic Tomography System for Small Animals," Optics Express, 17(13): 10489-10498 (2009).
Gateau, J. et al., "Three-Dimensional Optoacoustic Tomography Using a Conventional Ultrasound Linear Detector Array: Whole-Body Tomographic System for Small Animals," Medical Physics, 40(1): 013302-013311 (2013).
Guo, L. et al., "On the Speckle-Free Nature of Photoacoustic Tomography," Medical Physics, 36(9): 4084-4088 (2009).
Heijblom, M. et al., "Visualizing Breast Cancer Using the Twente Photoacoustic Mammoscope: What do we Learn from Twelve new Patient Measurements?," Optics Express, 20(11): 11582-11597 (2012).
Huang, B. et al., "Improving Limited-View Photoacoustic Tomography with an Acoustic Reflector," Journal of Biomedical Optics, 18(11): 110505 (2013).
Jensen, J. A., "Field: A Program for Simulating Ultrasound Systems," Medical & Biological Engineering & Computing, 34: 351-352 (1996).
Ke, H. et al., "Performance Characterization of an Integrated Ultrasound, Photoacoustic, and Thermoacoustic Imaging System," Journal of Biomedical Optics, 17(5): 056010 (2012).
Kruger, R. et al., "Hypr-Spectral Photoacoustic CT for Preclinical Imaging," Proceedings of SPIE, 7177: 71770F (2009).
Kruger, R. A. et al., "Photoacoustic Angiography of the Breast," Medical Physics, 37(11): 6096-6100 (2010).
Ku, G. et al., "Deeply Penetrating Photoacoustic Tomography in Biological Tissues Enhanced with an Optical Contrast Agent," Optics Letters, 30(5): 507-509 (2005).
Kuhl, C. "The Current Status of Breast MR Imaging," Radiology, 244(2): 356-378 (2007).
Lehman, C. D. et al., "Cancer Yield of Mammography, MR, and US in High-Risk Women" Radiology 244(2): 381-388 (2007).
Lehman, C. D. et al., "MRI Evaluation of the Contralateral Breast in Women with Recently Diagnosed Breast Cancer," New England Journal of Medicine, 356(13): 1295-1303 (2007).
Li, C. et al., "Real-Time Photoacoustic Tomography of Cortical Hemodynamics in Small Animals," Journal of Biomedical Optics, 15(1): 010509 (2010).
Li, M-L et. al., "Simultaneous Molecular and Hypoxia Imaging of Brain Tumors In Vivo Using Spectroscopic Photoacoustic Tomography," Proceedings of the IEEE, 96(3): 481-489 (2008).
Liu, B. et al., "Phantom and in-vivo Measurements of Hemoglobin Concentration and Oxygen Saturation using PCT-S Small Animal Scanner," Proceedings of SPIE, 6437: 64371X (2007).
Maaβ, H. et al., "Noninvasive Measurement of Elastic Properties of Living Tissue." In Control Conference (ECC), 1999 European, IEEE, pp. 2465-2470 (1999).
Manohar, S. et al., "The Twente Photoacoustic Mammoscope: System Overview and Performance," Physics in Medicine and Biology, 50: 2543-2557 (2005).
Nass et al., "Mammography and Beyond: Developing Technologies for the Early Detection of Breast Cancer," Institute of Medicine National Research Council, National Academy Press, 2001 (311 pages).
Pan, D. et al., "Photoacoustic Sentinel Lymph Node Imaging with Self-Assembled Copper Neodecanoate ganoparticles," ACS Nano, 6(2): 1260-1267 (2012).
Pramanik, M. et al., "Design and Evaluation of a Novel Breast Cancer Detection System Combining Both Thermoacoustic (TA) and Photoacoustic (PA) Tomography," Medical Physics, 35(6): 2218-2223 (2008).
Razansky, D. et al., "Multispectral Opto-Acoustic Tomography of Deep-Seated Fluorescent Proteins in vivo," Nature Photonics, 3(7), 412-417 (2009).
Razansky, D. et al., "Volumetric Real-Time Multispectral Optoacoustic Tomography of Biomarkers," Nature Protocols, 6(8): 1121-1129 (2011).

(56) References Cited

OTHER PUBLICATIONS

Scheunders, P. "Local Mapping for Multispectral Image Visualization," Image and Vision Computing, 19(13): 971-978 (2001).
Siegel, R. et al., "Cancert Statistics, 2012," CA Cancer Journal for Clinicians, 62(1): 10-29 (2012).
Song, K. H., et al., "Noninvasive Photoacoustic Imaging of the Thoracic Cavity and the Kidney in Small and Large Animals," Medical Physics, 35(10): 4524-4529 (2008).
Wang, L. V., et al., "Boundary Conditions in Photoacoustic Tomography and Image Reconstruction," Journal of Biomedical Optics, 12(1): 014027 (2007).
Wang, L.V., "Multiscale Photoacoustic Microscopy and Computed Tomography," Nat. Photonics, 3(9): 503-509 (2009).
Wang, L V. et al., "Photoacoustic Tomography: In Vivo Imaging from Organelles to Organs," Science, 335: 1458-1462 (2012).
Xia, J. et al., "Three-Dimensional Photoacoustic Tomography Based on the Focal-Line Concept," Journal of Biomedical Optics, 16(9): 090505 (2011).
Xia, J. et al., "Whole-Body Ring-Shaped Confocal Photoacoustic Computed Tomography of Small Animals in vivo," Journal of Biomedical Optics, 17(5): 050506 (2012).
Xu, M et al., "Photoacoustic Imaging in Biomedicine," Review of Scientific Instruments, 77(4): 041101 (2006).
Xu, M. et al. "Universal Back-Projection Algorithm for Photoacoustic Computed Tomography," Physical Review E, 71 (1): 016706 (2005).
Xu, Y. et al., "Reconstructions in Limited-View Thermoacoustic Tomography," Medical Physics, 31(4), 724-733 (2004).
Yang, D. et al., "Fast Full-View Photoacoustic Imaging by Combined Scanning with a Linear Transducer Array," Optics Express, 15(23): 15566-15575 (2007).
Yao, J., et al. "In vivo Photoacoustic Imaging of Transverse Blood Flow by Using Doppler Broadening of Bandwidth," Opttics Letters, 35(9): 1419-1421 (2010).
Yao, J. et al., "Label-Free Oxygen-Metabolic Photoacoustic Microscopy in vivo," Journal of Biomedical Optics, 16(7): 076003 (2011).
Zhang, H. F. et al., "Functional Photoacoustic Microscopy for High-Resolution and Noninvasive in vivo Imaging," Nature Biotechnology 24(7): 848-851 (2006).
Wang, X et al., "Three-Dimensional Laser-Induced Photoacoustic Tomography of Mouse Brain with the Skin and Skull Intact," Optics Letters, 28(19), 1739-1741 (2003).
Kitai, T. et al., "Photoacoustic Mammography: Initial Clinical Results," Breast Cancer, 21(2): 146-153 (2012).

* cited by examiner

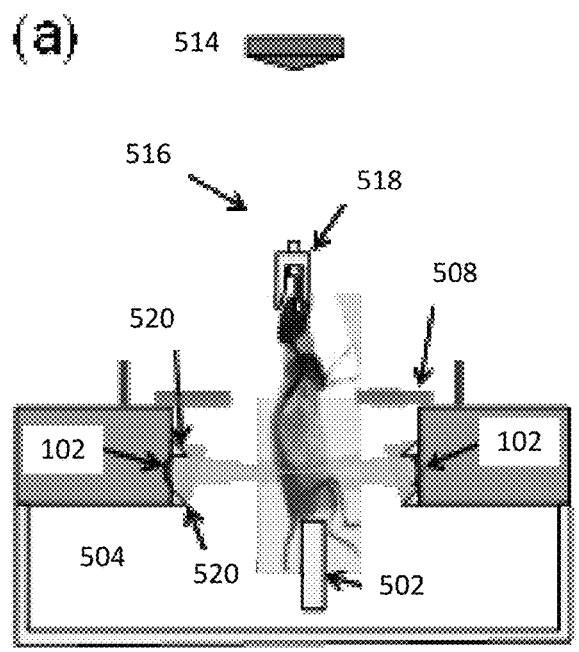
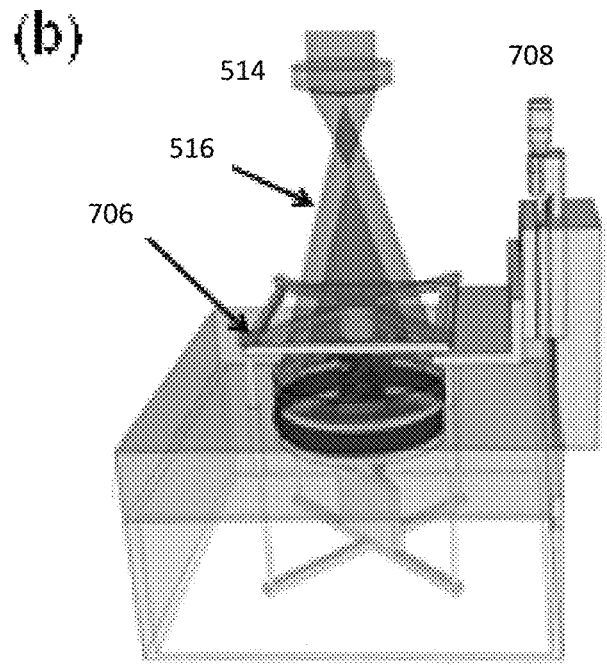
FIG. 5A  FIG. 5B
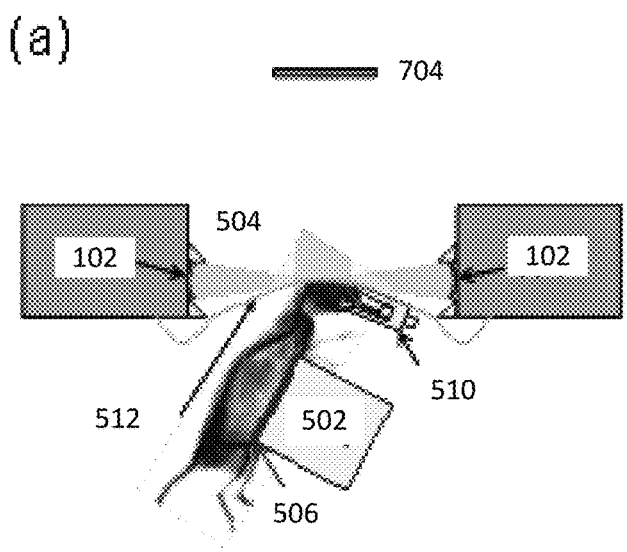
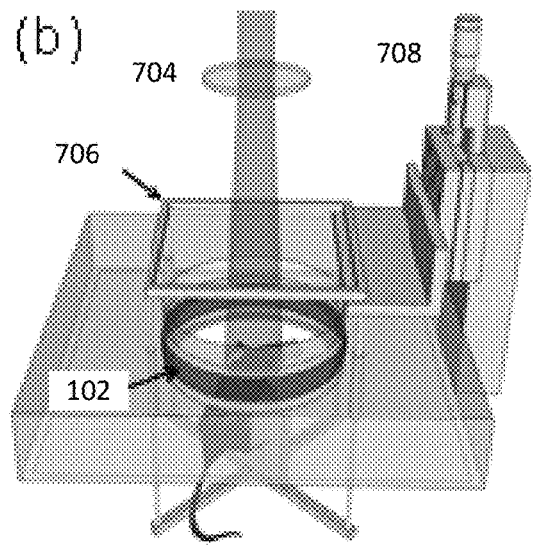
FIG. 6A  FIG. 6B

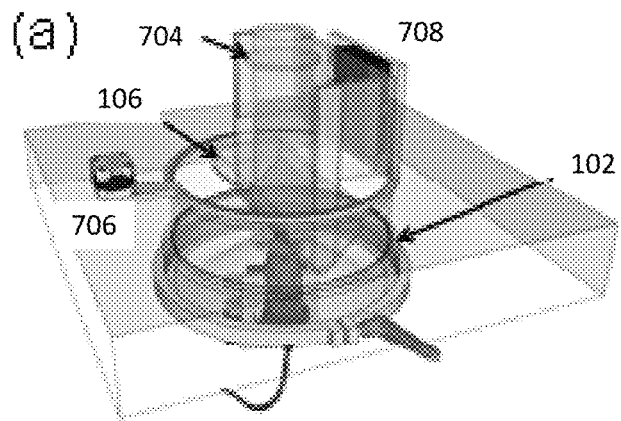 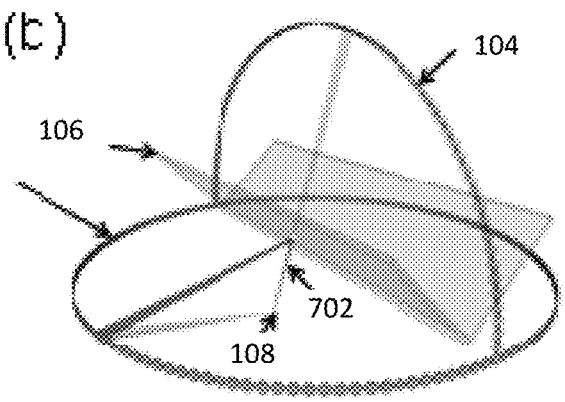
FIG. 7A      FIG. 7B
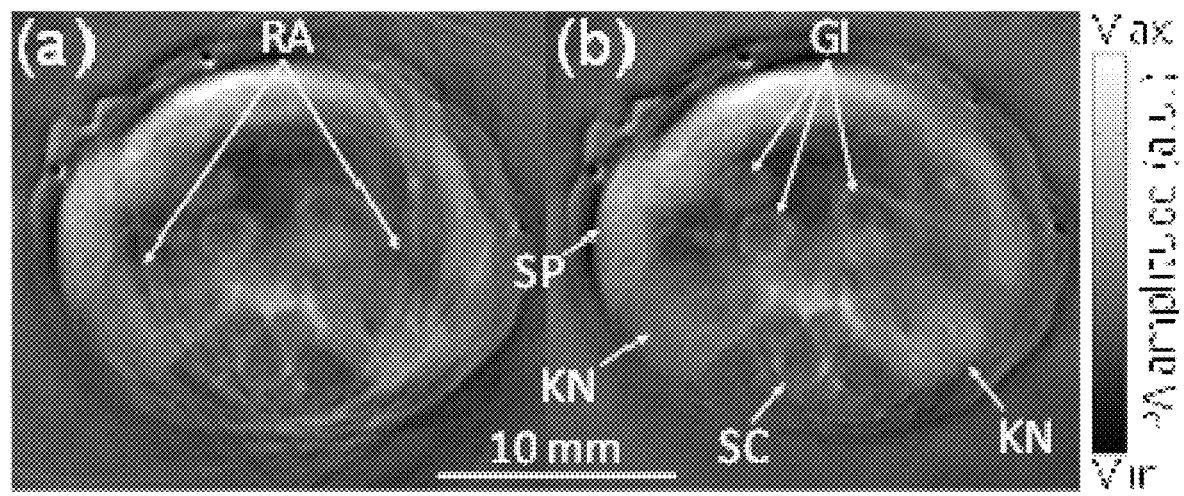
FIG. 8A      FIG. 8B

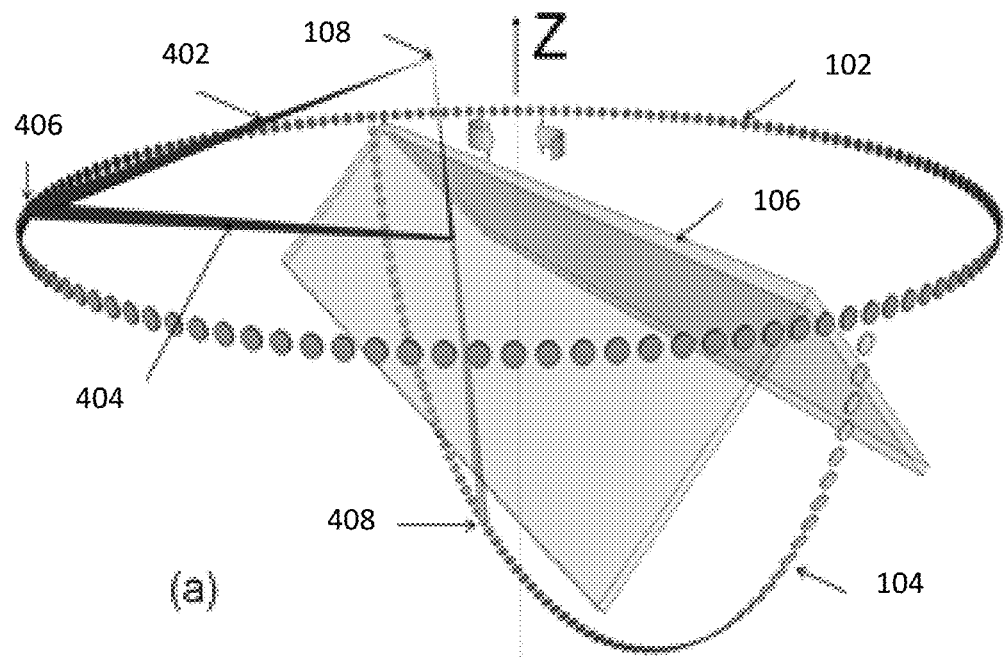
FIG. 12A
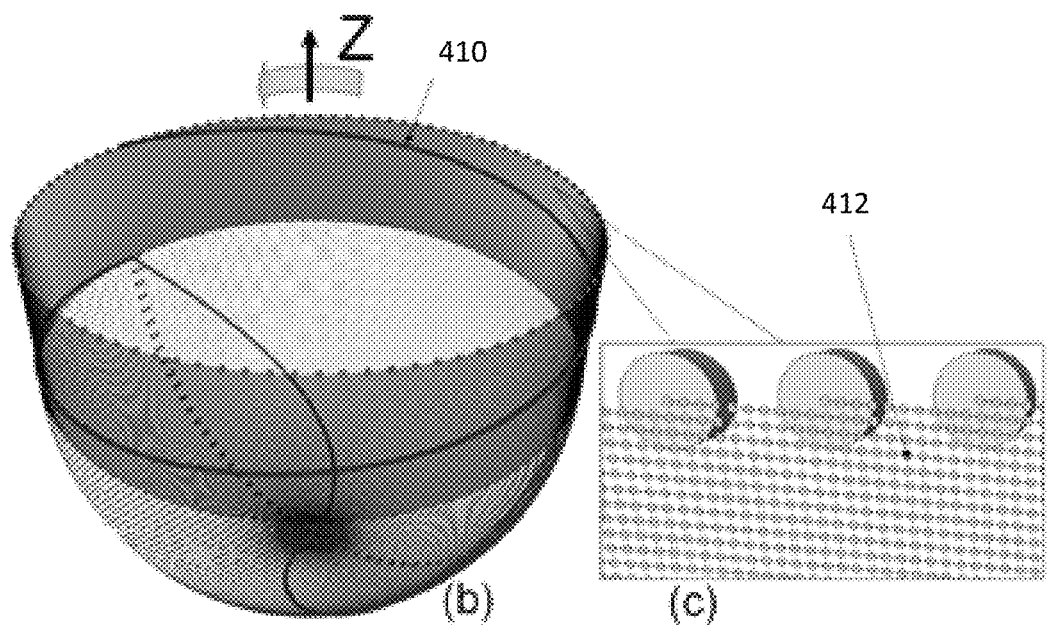
FIG. 12B   FIG. 12C

PHOTOACOUSTIC COMPUTED TOMOGRAPHY WITH A BIPLANAR ACOUSTIC REFLECTOR

CROSS-REFERENCE TO RELATED APPLICATIONS

This application is a 35 U.S.C. § 371 national stage application of PCT Application No. PCT/US2014/065195, filed Nov. 12, 2014, which claims the benefit of U.S. Provisional Application No. 61/902,918 filed on Nov. 12, 2013, both of which are incorporated herein by reference in their entirety.

GOVERNMENTAL RIGHTS IN THE INVENTION

This invention was made with government support under Grant No. R01 EB016963 awarded by National Institutes of Health. The government has certain rights in the invention.

FIELD OF THE INVENTION

The invention generally relates to systems and methods for improving limited-view photoacoustic tomography with an acoustic reflector.

BACKGROUND OF THE INVENTION

Photoacoustic tomography (PAT) provides high-resolution biomedical images beyond the optical diffusion limit by combining optical absorption contrast and ultrasonic spatial resolution. To obtain high-quality images, specialized full-ring transducer arrays may be used for full-view detection, but may be relatively expensive compared to linear arrays and may not be as easily integrated with ultrasound systems. The versatility and real-time imaging capability of commercial linear array transducers make them widely used in clinical ultrasound and photoacoustic imaging systems and devices. While commercial linear arrays are readily available, they often suffer from limited-view problems, and the detectable structure is sensitive to the orientations and positions of the probes. For instance, acoustic waves traveling at a grazing angle to the transducer surface are typically difficult to detect.

To overcome this limitation of linear array transducers, many methods have been proposed. One previous method circularly or semi-circularly scanned a linear array to achieve full-view or half-view PAT. However, these methods require time-consuming mechanical scanning. Another method proposed the use of speckle noise to derive PAT. This method required solution of Green's function and has been demonstrated only in simulations to date. Another method utilized artificial backscatters as virtual transducers. However, systems making use of this method still include circular scanning with a single-element transducer, and modeling the backscattered signals may be complicated. Limited-view problems may also be ameliorated using advanced image reconstruction algorithms; however, these image reconstruction methods are typically computationally intensive and time-consuming. In addition, it has been proposed to use acoustic reflectors at either end of, and perpendicular to, a linear array transducer to generate an infinitely wide virtual array, but this method has only been demonstrated in simulations to date A need exists for a high resolution PAM system that makes use of linear array transducers and other transducer configurations that overcomes the limitations inherent to the transducers without excessive impact on imaging time or requiring computationally challenging image reconstruction methods.

SUMMARY OF THE INVENTION

In an aspect, the present disclosure provides a photoacoustic imaging system including at least one ultrasound transducer array and at least one planar acoustic reflector situated on opposite sides of a planar imaging region. The at least one ultrasound transducer array includes a plurality of ultrasound transducers, each ultrasound transducer configured to receive one or more photoacoustic waves generated by at least one photoacoustic source within the planar imaging region. The at least one planar acoustic reflector is configured to reflect at least a portion of the one or more photoacoustic waves to produce at least one reflected photoacoustic wave propagating toward the at least one ultrasound transducer array. The one or more photoacoustic waves include at least one direct photoacoustic wave propagating from the at least one photoacoustic source to the at least one transducer array, the at least one reflected photoacoustic wave, and any combination thereof.

The at least one ultrasound transducer array is chosen from any one or more of: a linear array, a half-ring array, and a full ring array. The at least one ultrasound transducer array is chosen from a focused transducer array, at least one unfocused ultrasound transducer array, or any combination thereof. The at least one ultrasound transducer array may be the at least one focused ultrasound transducer array. The system may further include an optics device to direct at least one light pulse suitable for photoacoustic imaging into the planar imaging region. The optics device is chosen from: a diffuser to deliver a diffuse light pulse perpendicular to the planar imaging region or a conical lens and a ring mirror to produce a planar light pulse within the planar imaging region. The at least one ultrasound transducer array may be the at least one unfocused ultrasound transducer array and the optics device may be the conical lens and the ring mirror. The system may further include a translation stage operatively coupled to the at least one ultrasound transducer array, the at least one planar acoustic reflector, and the optics device to move the planar imaging region in a direction perpendicular to the planar imaging region. The at least one planar acoustic reflector is operatively coupled to a motor to rotate the at least one planar acoustic reflector about an axis perpendicular to the planar imaging region. The at least one ultrasound transducer array may be a full ring array operatively coupled to the motor to rotate the at least one ultrasound transducer array about an axis perpendicular to the planar imaging region. The at least one acoustic reflector is constructed from a material chosen from: borosilicate glass, sapphire, protected $MgF_2$ crystals, or fused silica plates. The at least one ultrasound transducer array may be the linear array and the at least one planar acoustic reflector is situated perpendicular to the planar imaging region and is further situated at a 45° angle relative to the linear array. The at least one ultrasound transducer array may be the half-ring array; the at least one planar acoustic reflector further includes an edge situated along a diameter of the at least one ultrasound transducer array; and the at least one planar acoustic reflector is further situated at a 45° angle relative to the planar imaging region.

In another aspect, the present disclosure provides a method of obtaining a photoacoustic image of a subject within a planar imaging region. The method includes detecting at least two photoacoustic waves generated by at least one photoacoustic source within the planar imaging region using an ultrasound transducer array. The at least two photoacoustic waves include at least one direct photoacoustic wave propagating from the at least one photoacoustic source to the ultrasound transducer array; and at least one reflected photoacoustic wave reflected to the ultrasound transducer array using an acoustic reflector situated on a side of the planar imaging region opposite to the ultrasound transducer array.

The method may further include recording a flight time for each of the at least two photoacoustic waves. The flight time may be a time elapsed between a delivery of a light pulse used to elicit the at least two photoacoustic waves and the detection of each of the at least two photoacoustic waves. The method may further include locating each photoacoustic source by: estimating a distance between each photoacoustic source and each transducer in the ultrasound transducer array by dividing the flight time by a speed of sound within the planar imaging region for each photoacoustic wave detected by each transducer in the ultrasound transducer array; for each direct photoacoustic wave, locating a corresponding photoacoustic source along a detection axis of each transducer at the estimated distance; and for each reflected photoacoustic wave, locating the corresponding photoacoustic source at the estimated distance along a virtual detection axis of a virtual transducer in a virtual ultrasound transducer array. The estimated distance is a summation of a first separation distance between the photoacoustic source and a location on the acoustic reflector and a second separation distance between the location on the acoustic reflector and the transducer in the ultrasound transducer array corresponding to the virtual transducer. The ultrasound transducer array is a linear array, the at least one planar acoustic reflector is situated perpendicular to the planar imaging region and is further situated at a 45° angle relative to the linear array, and the virtual array is situated perpendicular to the linear array and at a 45° angle relative to the acoustic reflector.

In an aspect, the ultrasound transducer array is a full ring array; the at least one planar acoustic reflector further includes an edge situated along a diameter of the full ring array; the at least one planar acoustic reflector is further situated at a 45° angle relative to the planar imaging region; and the virtual array is a half-ring array situated within a plane perpendicular to the planar imaging region and intersecting the planar imaging region at a diameter of the full ring array. The method may further include obtaining photoacoustic images in at least two different planar imaging regions by translating the ultrasound transducer array and the acoustic mirror in a direction perpendicular to the planar imaging region. The method may further include obtaining a three-dimensional photoacoustic image of the subject by combining the photoacoustic images obtained in at least two different planar imaging regions.

The method may further include obtaining multiple photoacoustic images by rotating the planar acoustic reflector about an axis coincident with a centerline axis of the full ring array. The method may further include rotating the full ring array about the axis coincident with the centerline axis of the full ring array. The method may further include obtaining photoacoustic images in at least two different planar imaging regions by translating the ultrasound transducer array and the acoustic mirror in a direction perpendicular to the planar imaging region. The method may further include obtaining a three-dimensional photoacoustic image of the subject by combining the photoacoustic images obtained in at least two different planar imaging regions.

BRIEF DESCRIPTION OF THE DRAWINGS

The following figures illustrate various aspects of the disclosure.

FIG. 3A is a photograph of the phantom. FIG. 3B is an image of the leaf skeleton phantom acquired without the presence of the acoustic reflector. FIG. 3C is an image of the phantom acquired with the presence of the reflector but reconstructed without incorporating data from the virtual array. FIG. 3D is an image of the phantom acquired with the presence of the acoustic reflector and reconstructed with data from the virtual array incorporated.

FIG. 5A is a front view schematic of an animal imaging system. FIG. 5B is an isometric view schematic of the animal imaging system.

FIG. 6A is a front view schematic of a brain imaging system. FIG. 6B is an isometric view schematic of the brain imaging system.

FIG. 7A is an isometric schematic illustration of a 2π-solid-angle PACT imaging system that includes an acoustic reflector. FIG. 7B is an isometric schematic illustration of the physical and virtual arrays when the acoustic reflector is present.

FIG. 8A is an in vivo cross-sectional PACT images of an athymic mouse using a full-time image reconstruction algorithm. FIG. 8B is an in vivo cross-sectional PACT images of an athymic mouse using a half-time image reconstruction algorithm. No acoustic reflector was incorporated into the system used to obtain the images of FIGS. 8A and 8B.

FIG. 10A was obtained before the dye injection. FIGS. 10B, 10C, and 10D are photoacoustic image differences relative to the pre-injection image of FIG. 10A at 32 s (FIG. 10B), 56 s (FIG. 10C), and 80 s (FIG. 10D) post-injection times, respectively.

FIG. 12A is a schematic illustration of the virtual arrays formed by an acoustic reflector. FIG. 12B is a schematic illustration of the spatial coverage by the transducer array (cylinder) and the virtual array (cap), where the spiral is the trace of a single element during mechanical scanning. FIG. 12C is an illustration of the spatial coverage with one half wavelength pitch by the aperture, where the disks represent transducer array elements.

Corresponding reference characters and labels indicate corresponding elements among the views of the drawings. The headings used in the figures should not be interpreted to limit the scope of the claims.

DETAILED DESCRIPTION

Figure 1A:
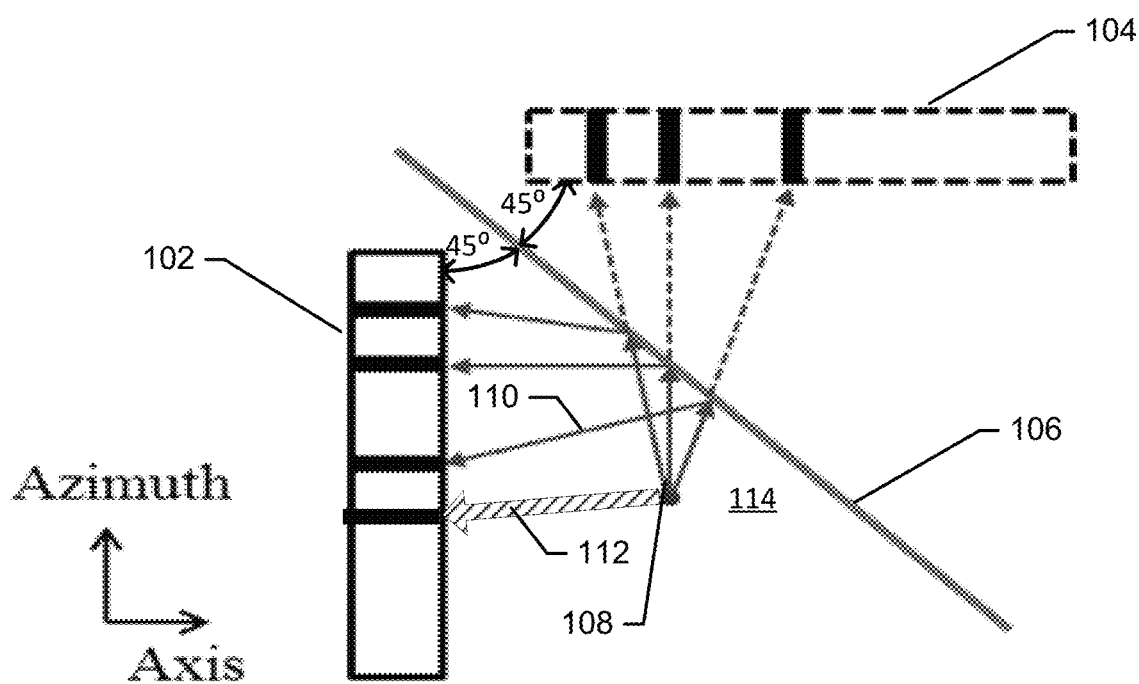
FIG. 1A is a top view of an arrangement of a linear transducer array and an acoustic reflector in a water tank in a prototype imaging system.

Provided herein are methods and systems for improving limited-view photoacoustic tomography systems and devices using an acoustic reflector. The systems and method may provide a simple and direct approach to enhance the detection view of a linear array photoacoustic (PA) imaging system. The system and method may utilize an acoustic reflector to form a virtual array that produces signals used in image reconstruction to overcome the limited-view problem of existing photoacoustic systems. In an aspect, the acoustic reflector may be a 45-degree acoustic reflector. Without being limited to any particular theory, the acoustic reflector may form a virtual array oriented perpendicular to the physical transducer array, resulting in a doubling of the area of detection.

I. Photoacoustic Imaging System with Acoustic Reflector

In various aspects, a system for photoacoustic imaging with an acoustic reflector includes a photoacoustic imaging system with an acoustic reflector used to form a virtual array. In an aspect, the present disclosure provides a photoacoustic imaging system that may include at least one ultrasound transducer array and at least one planar acoustic reflector situated on opposite sides of a planar imaging region. The at least one ultrasound transducer array may include a plurality of ultrasound transducers. Each ultrasound transducer may be configured to receive one or more photoacoustic waves generated by at least one photoacoustic source within the planar imaging region. In an aspect, the at least one planar acoustic reflector may be configured to reflect at least a portion of the one or more photoacoustic waves to produce at least one reflected photoacoustic wave propagating toward the at least one ultrasound transducer array. The one or more photoacoustic waves may include at least one direct photoacoustic wave propagating from the at least one photoacoustic source to the at least one transducer array, the at least one reflected photoacoustic wave, and any combination thereof.

By using an acoustic reflector, the detection view of a photoacoustic imaging system may be doubled. The use of an acoustic reflector to form a virtual array as disclosed herein may have advantages over physically shifting and rotating the transducer array. The system in this aspect may not require any mechanical scanning, thereby shortening the imaging time. Further, the acoustic reflector may be optically transparent, thereby allowing more flexible light illumination schemes.

In various aspects, the system may include a photoacoustic imaging system and an acoustic reflector. Non-limiting examples of imaging systems with which the acoustic reflector may be used include photoacoustic tomography (PAT), photoacoustic computed tomography (PACT), ultrasonic computed tomography (USCT), or any other imaging modality known in the art that receives an acoustic signal. In an aspect, full-view USCT and PACT may be combined. The acoustic reflector may improve the detection view of the imaging system.

The photoacoustic imaging system may include at least one ultrasound transducer array. Transducer arrays may include but are not limited to linear arrays, full-ring arrays, half-ring arrays, and any other commercially available transducer array. In one aspect, a full-ring transducer may be used in combination with an acoustic reflector. In this aspect, brain imaging may provide nearly isotropic spatial resolution. The at least one ultrasound transducer array is chosen from a focused transducer array, at least one unfocused ultrasound transducer array, or any combination thereof. The at least one ultrasound transducer array may be the at least one focused ultrasound transducer array. In another aspect, the system may include two or more ultrasonic transducer arrays. In this aspect, a first transducer array may be focused and a second transducer array may be unfocused.

The system may further include an optics device to direct at least one light pulse suitable for photoacoustic imaging into the planar imaging region. The optics device may include, but is not limited to, a diffuser to deliver a diffuse light pulse perpendicular to the planar imaging region or a conical lens and a ring mirror to produce a planar light pulse within the planar imaging region. The at least one ultrasound transducer array may be the at least one unfocused ultrasound transducer array and the optics device may be the conical lens and the ring mirror. The system may further include a translation stage operatively coupled to the at least one ultrasound transducer array, the at least one planar acoustic reflector, and the optics device to move the planar imaging region in a direction perpendicular to the planar imaging region. In an aspect, the at least one planar acoustic reflector may be operatively coupled to a motor to rotate the at least one planar acoustic reflector about an axis perpendicular to the planar imaging region.

In an aspect, the at least one ultrasound transducer array may be a full ring array operatively coupled to the motor to rotate the at least one ultrasound transducer array about an axis perpendicular to the planar imaging region. In another aspect, the at least one ultrasound transducer array may be a linear array and the at least one planar acoustic reflector may be situated perpendicular to the planar imaging region and may be further situated at a 45° angle relative to the linear array. In another aspect, the at least one ultrasound transducer array may be the half-ring array. In this aspect, the at least one planar acoustic reflector may further include an edge situated along a diameter of the at least one ultrasound transducer array and the at least one planar acoustic reflector may be further situated at a 45° angle relative to the planar imaging region.

Figure 1B:
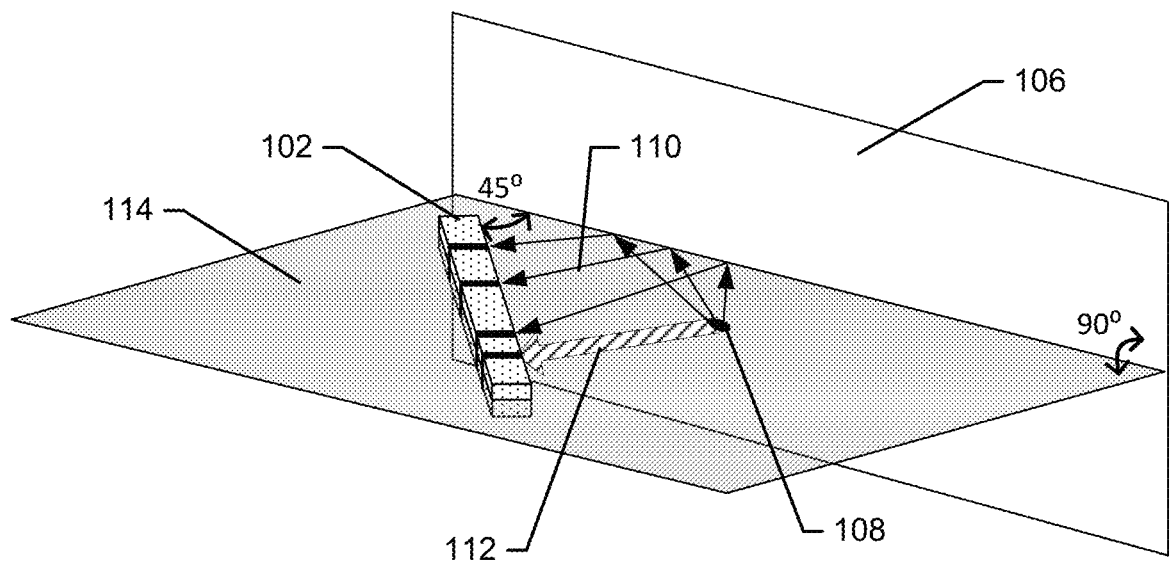
FIG. 1B is a perspective view of the prototype imaging system illustrated in FIG. 1A.

FIG. 1A and FIG. 1B are top view and perspective view illustrations, respectively, of a transducer array 102, a virtual array 104, and an acoustic reflector 106 in a system for photoacoustic imaging with an acoustic reflector. In an aspect, a source 108 within a planar imaging region 114 may emit photoacoustic signals, where each photoacoustic signal may either be a direct photoacoustic signal 112 detected directly by the transducer array 102 or a reflected photoacoustic signal 110 reflected by the acoustic reflector 106, where the reflected beam 110 may be detected by the transducer array 102 to generate a virtual array 104.

In an aspect, the ultrasonic transducer array 102 may range from about 10 cm to about 25 cm in diameter. In various aspects, the diameter of the transducer array may range from about 2 cm to about 10 cm, from about 5 cm to about 15 cm, from about 10 cm to about 20 cm, from about 15 cm to about 25 cm, and from about 20 cm to about 30 cm. In an aspect, the about 10 cm to about 25 cm diameter may allow adequate space for mounting optical components and accommodating subjects or parts of subjects to be imaged using the system including, but not limited to, small animals or humans. In another aspect, the transducer array 102 may be equipped with about 256 elements to about 512 elements. In various aspects, the transducer array 102 may be a 256 element linear array, a 256 element half-ring array, a 512 element full-ring array, or combinations thereof. The central frequency of the transducer array 102 may range from about 5 MHz to about 25 MHz. In various aspects, the central frequency of the transducer array may range from about 5 MHz to about 15 MHz, from about 10 MHz to about 20 MHz, from about 15 MHz to about 25 MHz, and from about 20 MHz to about 30 MHz.

Excitation may be provided by a Ti-sapphire laser tunable from about 700 nm to about 900 nm. With the combination of a conical lens and an optical condenser, a ring-shaped light beam may be projected around the animal body at an about 60° incident angle.

The transducer array may include circular elements with a diameter of 1.2 mm, corresponding to about 2 wavelengths of the acoustic signals. The diameter of each transducer element may tradeoff between equivalent pressure sensitivity, which is roughly proportional to the diameter of the transducer element, and the reduction of imaging resolution for peripheral areas, which may be outside of the transducer element's acceptance angle. Without being limited to any particular theory, the two wavelength element size results in less than two fold resolution reduction for the very peripheral areas (near the breast surface).

The transducer array 102 may be connected to an ultrasound data acquisition system. In one aspect, a commercial 256-channel ultrasound acquisition system may be connected to the transducer array 102 of the system. The ultrasound transmission and reception may be controlled independently in every channel in this aspect. To evenly cover a full ring in data acquisition for each laser pulse, the array elements may be interlaced for data multiplexing in this aspect.

In various aspects, the acoustic reflector 106 may include, but is not limited to, borosilicate glass, sapphire, protected $MgF_2$ crystals, or fused silica plates. In an aspect, the fused silica plates may be situated perpendicular to one another. In an aspect, the acoustic reflector 106 may be optically transparent so that a light source of the photoacoustic system may pass through the acoustic reflector 106 to the subject. The acoustic reflector 106 may be made of any suitable material having a relatively high shear modulus, in which the critical angle for Rayleigh surface waves may be as small as about 12°. In one aspect, the acoustic reflector may be borosilicate glass plate, which has a critical angle for Rayleigh surface waves of about 26°. The borosilicate glass acoustic reflector may be about a quarter inch thick in one aspect. The glass plate may have a sound speed of about 5790 m/s for longitudinal waves and about 3420 m/s for shear waves. When the angle of incidence is greater than about 26° (the critical angle for Rayleigh surface waves), the incident PA waves may be completely reflected without distortion. For angles of incidence between 0° (perpendicular incidence) and a longitudinal critical angle of about 14°, about 80% of the pressure of the incident PA waves may be reflected also with essentially no phase change, but may have multiple delayed reflections due to reverberation. Reflection for angles of incident ranging from about 14° to about 26° may be more complicated by amplitude and phase changes with the angle. However, these effects may be neglected for purposes of image reconstruction. The acoustic reflector may be made less sensitive to PA wave incident angle by using materials with a higher shear modulus, including, but not limited to, sapphire in which the critical angle for Rayleigh surface waves may be as small as 12°.

In an aspect, the acoustic reflector 106 may be a 45° acoustic reflector, as illustrated in FIG. 1A and FIG. 1B. In various aspects, the acoustic reflector 106 may be at any angle which may reflect acoustic signals from a source in the subject to the transducer array 102 to create the virtual array 104. The transducer array and acoustic reflector orientations may be flexibly designed for other applications. Without being limited to a particular theory, to achieve at least a 180° detection angle, an array with a larger acceptance angle or multiple acoustic reflectors may be used.

Due to the inclusion of an external acoustic reflector in the system design, reflected wavefields may be recorded on a virtual capped-cylindrical aperture. However, only in-plane TOF measurements of forward scattered wavefields may be recorded in a series of parallel transverse planes. In an aspect, helical scanning of a 256-element unfocused full-ring transducer array coordinated with rotation of an acoustic reflector may provide a virtual capped-cylindrical aperture for an effectively full-view PACT configuration (>$2\pi$ sr solid angle in 3D) to achieve nearly isotropic spatial resolutions.

For small animal imaging in one aspect, the acoustic reflector may be implemented as an enclosing wall of an immersion tank. In this case, the real and virtual arrays may form a half-enclosed space for the object, which may improve the image quality substantially. For larger objects or subjects, the transducer array may be translated one or more steps in an azimuthal direction with a step size equal to the length of the array, and the imaging region may be enlarged accordingly. As demonstrated in Examples 2-5, both phantom and ex vivo images obtained by prototype systems demonstrated that the inclusion of an acoustic reflector in the imaging system provided a simple and easy approach to increase the detection view of linear array-based PAT, yielding higher-quality PA images.

II. Method for Photoacoustic Imaging with an Acoustic Reflector

In various aspects, a method for photoacoustic imaging with an acoustic reflector may include integrating an acoustic reflector with a transducer array to form a virtual array transducer for use in imaging systems making use of imaging methods including, but not limited to photoacoustic tomography (PAT), photoacoustic computed tomography (PACT), ultrasonic computed tomography (USCT), or any other imaging modality that receives and processes acoustic signals. In an aspect, the present disclosure provides a method of obtaining a photoacoustic image of a subject within a planar imaging region. The method may include detecting at least two photoacoustic waves generated by at least one photoacoustic source within the planar imaging region using an ultrasound transducer array. The at least two photoacoustic waves may include at least one direct photoacoustic wave propagating from the at least one photoacoustic source to the ultrasound transducer array and at least one reflected photoacoustic wave reflected to the ultrasound transducer array using an acoustic reflector situated on a side of the planar imaging region opposite to the ultrasound transducer array.

In another aspect, the method may include illuminating an area of interest in a subject with a light source, directly receiving, at a transducer array 102, acoustic signals generated by an acoustic source 108 in the area of interest 114, and receiving, at the transducer array 102, acoustic signals reflected by the acoustic reflector 106 to create a virtual array 104. In various aspects, the light source may be focused or unfocused and the ultrasound transducer array may be focused or unfocused. In an aspect the light source may be a laser.

In an aspect, the method may further include recording a flight time for each of the at least two photoacoustic waves. The flight time may include a time elapsed between a delivery of a light pulse used to elicit the at least two photoacoustic waves and the detection of each of the at least two photoacoustic waves. In another aspect, the method may further include locating each photoacoustic source by estimating a distance between each photoacoustic source and each transducer in the ultrasound transducer array by dividing the flight time by a speed of sound within the planar imaging region for each photoacoustic wave detected by each transducer in the ultrasound transducer array. For each direct photoacoustic wave, a corresponding photoacoustic source may be located along a detection axis of each transducer at the estimated distance. For each reflected photoacoustic wave, the corresponding photoacoustic source may be located at the estimated distance along a virtual detection axis of a virtual transducer in a virtual ultrasound transducer array. The estimated distance may be a summation of a first separation distance between the photoacoustic source and a location on the acoustic reflector and a second separation distance between the location on the acoustic reflector and the transducer in the ultrasound transducer array corresponding to the virtual transducer. In an aspect, the ultrasound transducer array may be a linear array, the at least one planar acoustic reflector may be situated perpendicular to the planar imaging region 114 and may be further situated at a 45° angle relative to the linear array 102, and the virtual array may be situated perpendicular to the linear array and at a 45° angle relative to the acoustic reflector, as illustrated in FIG. 1A and FIG. 1B.

In an aspect, the ultrasound transducer array may be a full ring array. The at least one planar acoustic reflector may further include an edge situated along a diameter of the full ring array. The at least one planar acoustic reflector may be further situated at a 45° angle relative to the planar imaging region. The virtual array may be a half-ring array situated within a plane perpendicular to the planar imaging region and intersecting the planar imaging region at a diameter of the full ring array. In another aspect, the method may further include obtaining photoacoustic images in at least two different planar imaging regions by translating the ultrasound transducer array and the acoustic mirror in a direction perpendicular to the planar imaging region. The method may further include obtaining a three-dimensional photoacoustic image of the subject by combining the photoacoustic images obtained in at least two different planar imaging regions.

In an aspect, the method may further include obtaining multiple photoacoustic images by rotating the planar acoustic reflector about an axis coincident with a centerline axis of the full ring array. In this aspect, the method may further include rotating the full ring array about the axis coincident with the centerline axis of the full ring array. The method may further include obtaining photoacoustic images in at least two different planar imaging regions by translating the ultrasound transducer array and the acoustic mirror in a direction perpendicular to the planar imaging region. The method may further include obtaining a three-dimensional photoacoustic image of the subject by combining the photoacoustic images obtained in at least two different planar imaging regions.

The acoustic reflector may be rotated to receive additional reflected acoustic signals. The rotational speed of the acoustic reflector may be determined by the number of elements in a transducer array and the desired frame rate. In one non-limiting example, the system may complete a scan in as little as about 5.12 s (=128/25). In an aspect, the frame rate may range from about 0.625 fps to about 45 fps. In various aspects, the frame rate may range from about 0.5 fps to about 10 fps, from about 5 fps to about 15 fps, from about 10 fps to about 20 fps, from about 15 fps to about 25 fps, from about 30 fps to about 40 fps, about 35 fps to about 45 fps, and about 40 fps to about 50 fps. In one aspect, USCT imaging may be performed at a frame rate of up to about 45 fps and PACT may be performed at a frame rate of up to about 25 fps.

The system may be used for whole body imaging of a subject in an aspect. The subject may include, but is not limited to, a human subject or a small animal subject. In other aspects, the system may also be used for imaging a portion of a subject including, but not limited to a trunk, a breast, or a brain of a subject.

In another aspect, the method may include rotating an ultrasound transducer array 102 about a region of interest in the z-direction along a spiral trajectory, rotating an acoustic reflector 106 through a sweep of about 180° around the region of interest, moving the ultrasound transducer array 102 a step, and rotating the acoustic reflector 106 through an additional sweep of about 180° around the region of interest. The rotation of the ultrasound transducer array 102 and the acoustic reflector 106 may create a three-dimensional image of the region of interest. The acoustic reflector creates a virtual array 104 for increasing the detection view of the photoacoustic imaging system.

In various aspects, the method may include acquiring images of a small animal. In one aspect, an unfocused transducer array included in the system as described herein above may be used to scan an animal's head in elevation over a larger distance, taking advantage of the wide acceptance angle of the unfocused transducer array.

In an aspect, the method may include breast imaging. In this aspect, the transducer array may be a half-ring or a full-ring transducer array. During imaging in this aspect the laser may be adjusted by a zoom lens assembly 330 (in FIGS. 11A and 11B) to illuminate either the whole breast or be directed to a smaller region of interest. To increase the view aperture for 3D imaging, an acoustic reflector 106 may be employed to form a virtual capped-cylindrical aperture.

The transducer array may move in the elevational (Z) direction to cover the whole compressed breast along a spiral trajectory. In an aspect, the transducer array 102 may move about 1.4 degrees in steps of about 0.14 degrees around a cylinder while moving along the cylinder in the Z direction with a step size of about 0.3 mm (FIG. 12B) by way of non-limiting example. The acoustic reflector (106) may be added and rotated over about 180 degrees around the Z-axis with an angle step of about 0.32 degrees. The transducer array may be rotated about 0.7 degrees, then the acoustic reflector may again rotate over about 180 degrees with an angle step of about 0.32 degree to finish a frame of 3D imaging.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Small-Animal Imaging

Small-animal whole-body imaging using the system may use a 512-element full-ring transducer array. Excitation was provided by a Ti-sapphire laser tunable from about 700 nm to about 900 nm. With the combination of a conical lens and an optical condenser, a ring-shaped light beam was projected around the animal body at an about 60° incident angle. The thickness of the light ring was about 5 mm, and the diameter may be sized to accommodate the cross-sectional diameter (about 2 cm) of the animal. The maximum light intensity at the surface of the animal was about 15 mJ/cm$^2$, which is below the ANSI safety limit at the chosen wavelength.

To cover a broad range of applications, two system configurations as illustrated in FIGS. 5A and 5B and FIGS. 6A and 6B were used for trunk and brain imaging. In FIGS. 5A and 5B, the system elements include 502: animal holder; 518: breathing mask; 504: heated coupling medium; 514: conical lens; 516: laser beam; 706: metal frame; 508: plastic ring; 520: ring-shaped mirror; 102: transducer array; and 708: translation stage. Both configurations share two switchable 256-element full-ring ultrasound transducer arrays. One array was cylindrically focused for dynamic 2D imaging, and the other array was unfocused for high-quality 3D imaging. The ultrasound transmitting and receiving was controlled by a commercial ultrasound acquisition system (V-1-128, Verasonics Inc.). Compared with the custom-built acquisition system in a prototype system, the Verasonics system provided several advantages: (a) more parallel data acquisition channels (128 vs. 64); (b) each channel is equipped with a large buffer memory (capable of storing 3.14 MegaSamples), allowing continuous sampling without transferring data to computer memory; and (c) ultrasonic transmitting and receiving was performed and controlled independently in every channel.

FIGS. 6A and 6B show a configuration of a brain imaging system. FIG. 6A is a schematic side view and FIG. 6B is a schematic isometric view of the brain imaging system. Elements of the brain imaging system include: an animal holder (502); a coupling medium (504); an engineered diffuser (704); a heating pad (506); a metal frame (706); a plastic ring (508); a transducer array (102); a tooth bar (510); a transparent membrane (512); and a translation stage (708).

To take full advantage of the high data acquisition speed, a 50-Hz pulsed laser system (Pump laser: Standard 600, Allied laser solutions; Dye laser: Credo-Dye-P, Newport) was employed with a wavelength tunable from 400 to 920 nm. With 2:1 data multiplexing, PACT was performed at 25 fps. USCT was conducted in both transmission and reflection modes using the system. Ultrasound pulses were fired sequentially over 128 evenly distributed elements of the transducer array (i.e., every other element). At each firing position, the transmitted/reflected waves will be detected by all of the 256 elements of the transducer array. The imaging speed may be limited by the speed of sound (SOS). For a 10-cm-diameter ring and 3-cm-diameter object, the wait time between pulse firings was about 86 µs (13 cm divided by the SOS in water, 1,500 m/s), rendering 45 fps with 128 firings (with 2:1 data multiplexing at each firing position). This frame rate may allow USCT and PACT to be interlaced, providing naturally co-registered images. The prototype and proposed systems are compared in Table 2.

The system for photoacoustic computed tomography imaging with an acoustic reflector was used to acquire images of a small animal. An unfocused transducer array included in the system as described herein above was used to scan an animal's head in elevation over a larger distance, taking advantage of the wide acceptance angle of the unfocused transducer array. A scan may provide a cylindrical aperture for PACT and USCT of the brain of an animal subject. An acoustic reflector as illustrated in FIGS. 7A and 7B may provide a wider elevational view aperture. FIGS. 7A and 7B are illustrations of a 2π-solid-angle PACT system that includes an acoustic reflector. FIG. 7A is a 3D schematic diagram of the system. FIG. 7B is an illustration of the orientation of the physical and virtual arrays when the acoustic reflector is present, where 106 is the acoustic reflector; 702 is the acoustic wave; 704 is the engineered diffuser; 706 is the metal frame; 108 is the source point; 102 is the transducer array; 708 is the translation stage; and 104 is two semicircular virtual arrays.

The small animal may be maintained in a position where the top of the head is at the same height as the array element. An acoustic reflector, consisting of two protected MgF$_2$ crystals perpendicular to each other, was fully immersed in the water. The position of the reflector may be adjusted or scanned in elevation through a translation stage (FIG. 7A). Because the refractive index of the MgF$_2$ crystal is close to that of water, the reflector may not refract the illumination light. However, in the presence of the hard boundaries between the crystals and water, incident ultrasonic waves may be reflected. Equivalently, the transducer array may be considered to be mirror-projected onto a vertical plane, to form two virtual half-ring arrays (FIG. 7B). By rotating the acoustic reflector continuously over 180 degrees about the vertical axis, a virtual hemispherical array may be formed, enabling a 2π-solid-angle aperture. The combination of vertical translation and rotation about the vertical axis may provide a capped-cylindrical aperture for PACT. Such a large detection view aperture may enhance the image quality significantly, especially in the elevational direction. In USCT, because of the curved skull, the incident acoustic waves may be reflected upward. The acoustic reflector may facilitate collection of these data, allowing more accurate recovery of incident acoustic waves, especially those waves reflected from the outer surface of the skull. The rotational speed of the acoustic reflector may be determined by the number of elements in half a ring and the desired frame rate. In one non-limiting example, the system may complete a scan in as little as about 5.12 s (=128/25).

The imaging speed of the animal imaging system may be influenced by the speed of the data acquisition system used to acquire and process the acoustic signals generated within the animal subject. A prototype animal imaging system that included a custom-made data acquisition system had a framing rate of about 0.625 fps. With the use of faster data acquisition systems, framing rates of up to about 25 fps or faster may be achieved, allowing the capture in real-time of physiological and/or neurological processes including, but not limited to brain dynamics, such as responses to stimulation.

Example 2

Linear Array

A commercially obtained Philips linear array was operated in B-mode to collect photoacoustic signals, a 45-degree acoustic reflector (glass) was used to form a virtual array, and a laser beam aligned orthogonally to the drawing illuminated the water tank from the top (not shown in the figure).

In addition to the conventional linear array, a quarter inch thick borosilicate glass plate (8476K72, McMaster-Carr, Los Angeles, Calif.) functioned as an acoustic reflector to form a virtual linear array. The glass plate had a sound speed of 5790 m/s for longitudinal waves and 3420 m/s for shear waves. When the angle of incidence was greater than 26° (the critical angle for Rayleigh surface waves in borosilicate glass), the incident PA waves were completely reflected without distortion. For angles of incidence between 0° (perpendicular incidence) and a longitudinal critical angle of 14°, about 80% of the pressure of the incident PA waves reflected with no phase change, but with multiple delayed reflections due to reverberation. Reflection of PA waves with incident angles ranging from about 14° to about 26° were even further distorted by amplitude and phase changes as a function of incidence angle. However, these distortions were not taken into account in reconstruction.

As illustrated in FIG. 1A and FIG. 1B, some PA waves were reflected by the acoustic reflector and detected by receiving elements (RE) of the physical array. According to the method of image reconstruction to satisfy the boundary condition imposed by the reflector, the same PA waves may be considered as detected by the elements RE' of a virtual array situated in an acoustic homogeneous medium without the reflector. Therefore, the system functionally consisted of two linear arrays that were mutually perpendicular to one another. The linear transducer array (L7-4, Philips Healthcare, Andover, Mass.) had 128 elements with a center frequency of 5.0 MHz, a receiving bandwidth of about 80%, a pitch of 0.3 mm, and an elevational height of 6 mm. The transducer array was cylindrically focused in the elevation, with a focal length of 25 mm.

The PA signals received by the transducer array were multiplexed and digitalized by a 64-channel commercial ultrasound system (V-1, Verasonics, Inc., Redmond, Wash.) with a sampling rate of 60 MHz. The hard boundary condition associated with the acoustic reflector was satisfied by directly assigning the received PA signals to the virtual array. The image was then reconstructed using the conventional filtered back-projection algorithm for an infinite medium without boundaries. To increase the signal-to-noise ratio, each image was obtained by averaging 64 repeated measurements, taking approximately 6.4 seconds to acquire an averaged image. For simplicity, top illumination was provided by a Q-switched Nd:YAG laser (LS-2137/2, LOTIS TII, Minsk, Belarus) with a pulse duration of less than 15 ns and a pulse repetition rate of 10 Hz. The 532 nm laser light was homogenized by an optical diffuser (EDC-5, RPC Photonics, Rochester, N.Y.), and the incident laser beam on the phantom/tissue surface was controlled to be less than the maximum permissible exposure set by the American National Standards Institute (ANSI) (20 mJ/cm$^2$). During the experiment, a 45-degree angle ruler was used to align the transducer array and the acoustic reflector. During image reconstruction, the position of the virtual array was numerically adjusted to yield the sharpest image. The axial, lateral, and elevational resolutions of the system were about 0.2 mm, 0.3 mm, and 1.6 mm respectively, obtained by measuring the point spread function from the cross-sectional images of human hairs, as described in Example 3.

Example 3

Hair Phantom

Figure 2A:
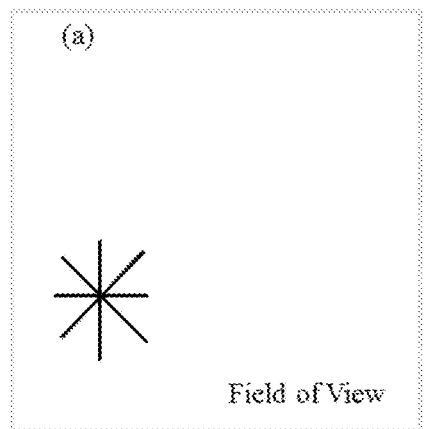
FIG. 2A is a diagram of a hair phantom used to assess the resolution of a prototype imaging system.
Figure 2B:
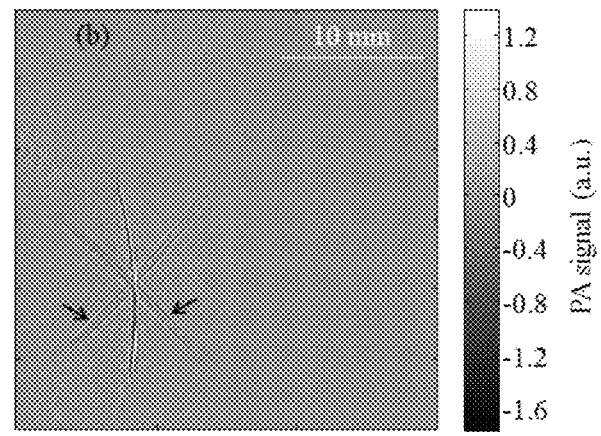
FIG. 2B is an image of the hair phantom acquired without the presence of the acoustic reflector.
Figure 2C:
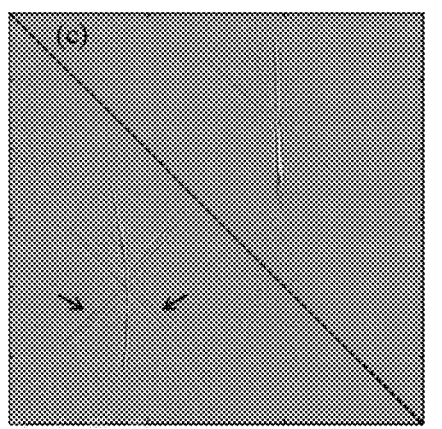
FIG. 2C is an image of the phantom acquired with the presence of the reflector but reconstructed without incorporating data from the virtual array.
Figure 2D:
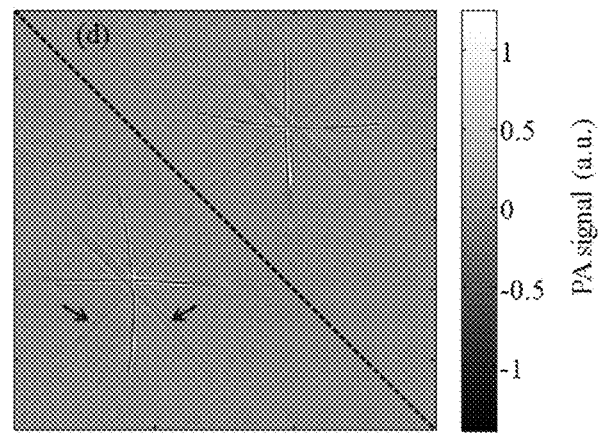
FIG. 2D is an image of the phantom acquired with the presence of the reflector and reconstructed with data from the virtual array incorporated.

To experimentally validate the reconstruction technique using the system described in Example 2, a phantom consisting of four human hairs was imaged using the system of Example 2 at different angles on the azimuth-axis plane (FIG. 2A) and the phantom image was reconstructed under different conditions. FIGS. 2A, 2B, 2C, and 2D show PAT images of a hair phantom. The dashed-line indicates the position of the acoustic reflector. FIG. 2B is an image acquired without the presence of the acoustic reflector. FIG. 2C is an image acquired with the presence of the reflector—as indicated by the dashed-line—but reconstructed without incorporating the virtual array. The linear array was unable to detect the horizontal hair, because the cylindrical PA wavefront from that hair propagated in the azimuth (vertical) direction and hence missed the physical array unless reflected using the acoustic reflector. The reconstruction incorporating data from the virtual array successfully overcame this problem (FIG. 2D) and all the hairs were visualized. While the vertical hair was imaged directly by the physical array, the horizontal hair was imaged by the virtual array. However, because of the limited acceptance angle of the array, the hairs oriented at ±45° (marked with solid arrows in FIGS. 2B, 2C, and 2D) appeared blurrier and weaker than the two horizontally and vertically aligned hairs. Based on the Field II ultrasound simulation program, the simulated acceptance angle (3 dB drop in one-way pressure profile at the distance of the elevational focus) of each element in the array was around ±28°. Therefore, PA signals traveling at a 45-degree angle of incidence from the hair were less detectable by the array.

Example 4

Leaf Skeleton

Figure 3A:
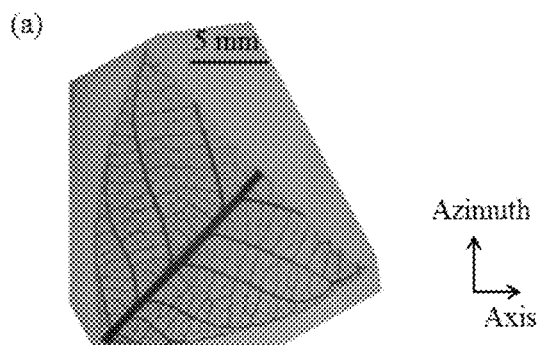
FIGS. 3A, 3B, 3C, and 3D show PAT images of a leaf skeleton phantom.
Figure 3B:
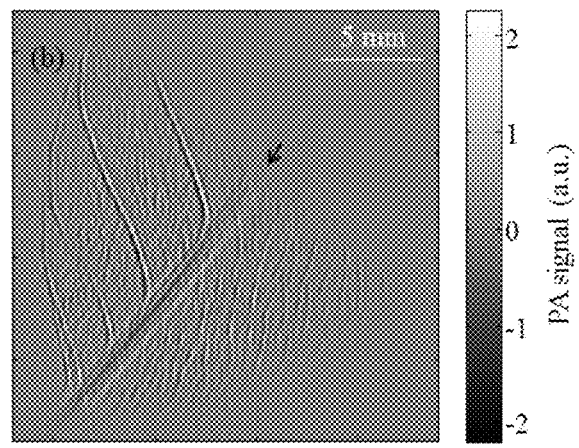
Figure 3C:
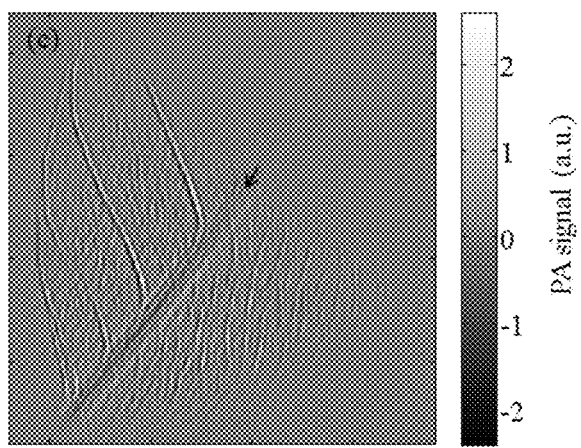
Figure 3D:
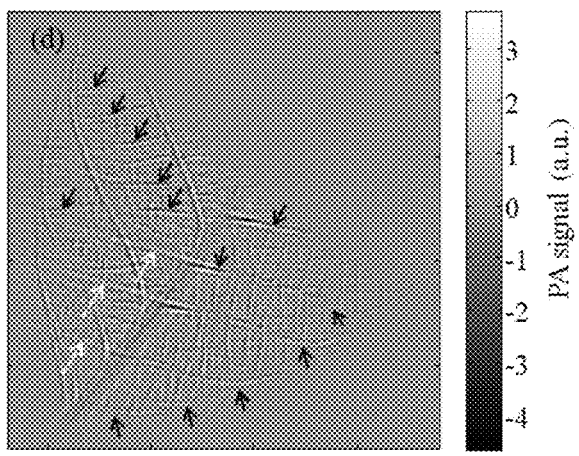

To experimentally validate the proposed method, a more complicated phantom, consisting of a leaf skeleton embedded in agar (FIG. 3A), was imaged using the system of Example 2. Agar had acoustic properties similar to those of the aqueous coupling medium. FIGS. 3B, 3C, and 3D show two-dimensional (2D) images acquired and reconstructed under different conditions using the system of Example 2. FIG. 3B is an image acquired without the presence of the acoustic reflector and FIG. 3C is an image acquired with the presence of the acoustic reflector but reconstructed without incorporating the virtual array data. In both images, the major skeletons on the lower-right side of the leaf were missing due to limited view. By incorporating the virtual array data, those missing skeletons were clearly recovered, as indicated by the arrows in FIG. 3D. The images of major skeletal elements with 45-degree orientation (marked with solid arrows in FIGS. 3B and 3C) were more blurred, possibly due to the limited acceptance angle of the transducer array. The streaking artifacts in FIG. 3D (indicated by white dashed arrows) may be attributed to insufficient view angle coverage.

Example 5

Mouse Ear

The efficacy of the proposed method was also evaluated by imaging an ear of a euthanatized C57BL/6 mouse (FIGS.

4A, 4B, 4C, and 4D) using the system of Example 2. The mouse ear was supported by an agar cylinder to maintain the ear in a flattened orientation within the azimuth-axis plane. The center of the ear was located approximately at the elevational focus of the array. Because of the strong blood absorption at 532 nm, major vasculature across the ear was visible.

Figure 4A:
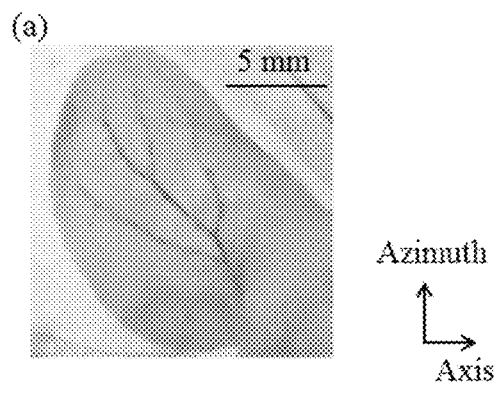
FIG. 4A is a photograph of a mouse ear.
Figure 4B:
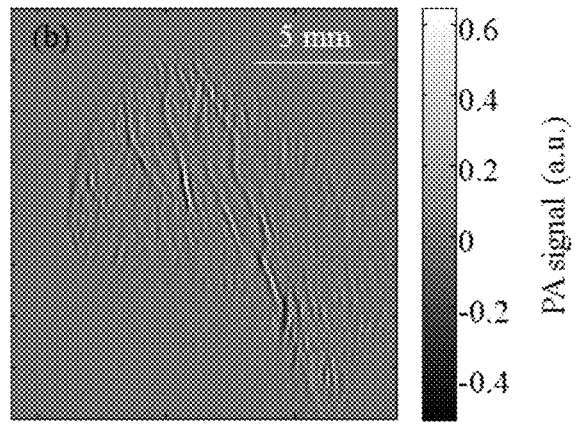
FIG. 4B is an image of the mouse ear acquired without the presence of the acoustic reflector.
Figure 4C:
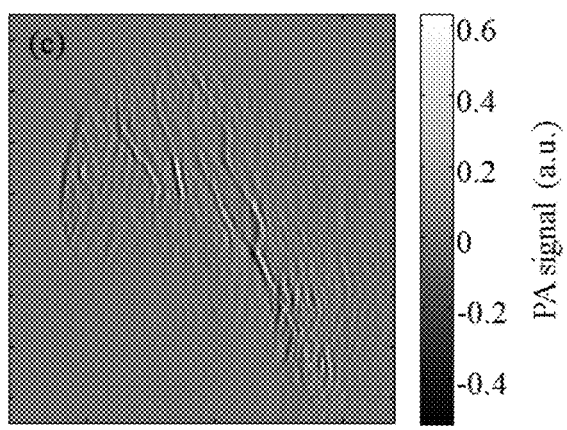
FIG. 4C is an image of the mouse ear acquired with the presence of the reflector but reconstructed without incorporating data from the virtual array.
Figure 4D:
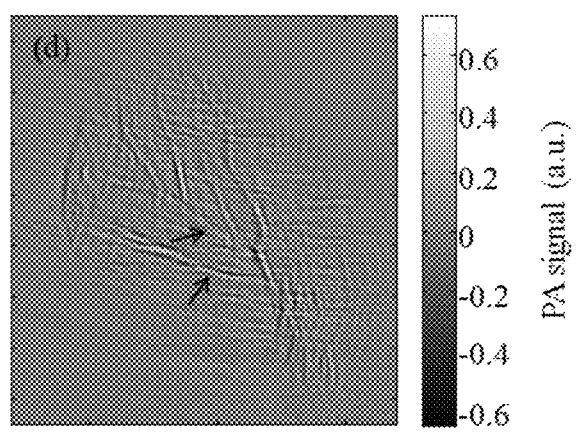
FIG. 4D is an image of the mouse ear acquired with the presence of the acoustic reflector and reconstructed with data from the virtual array incorporated.

FIGS. 4A, 4B, 4C, and 4D show ex vivo PAT images of a mouse ear. Again, without considering the virtual array, the presence of the acoustic reflector barely changes the 2D images (FIG. 4B vs. FIG. 4C), where two major vessels at small angles to the axial direction are missing due to limited view. When the reconstruction includes data from the virtual array, these two vessels can be visualized, as indicated by arrows in FIG. 4D. The advantages of the acoustic reflector and the increased detection view are well demonstrated in this ex vivo experiment. The small vertical artifacts in FIGS. 4B and 4C may be caused by streaking artifacts from insufficient views of small structures (such as tiny hairs, melanin, and small vessels) on the edge of the mouse ear. Similar artifacts appear horizontal when the virtual array is incorporated in the reconstruction (FIG. 4D). Also the curvature of the mouse ear may have caused some blurring artifacts.

Example 6

Mouse Brain

Figure 9A:
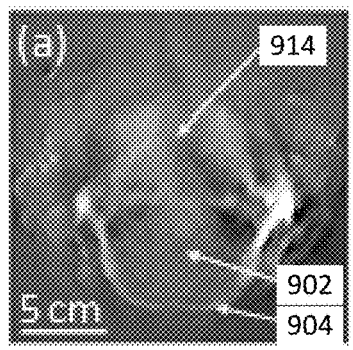
FIGS. 9A, 9B, 9C, 9D, 9E, and 9F are in vivo cross-sectional PACT images of athymic mice acquired noninvasively at various anatomical locations: the brain in coronal view (FIGS. 9A and 9B); the heart (FIGS. 9C and 9D); and the liver (FIGS. 9E and 9F).
Figure 9C:
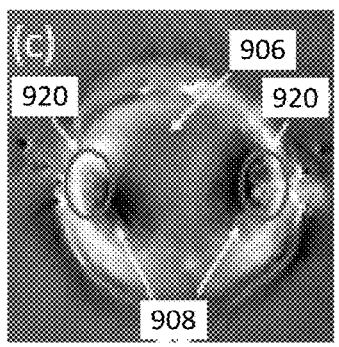
Figure 9E:
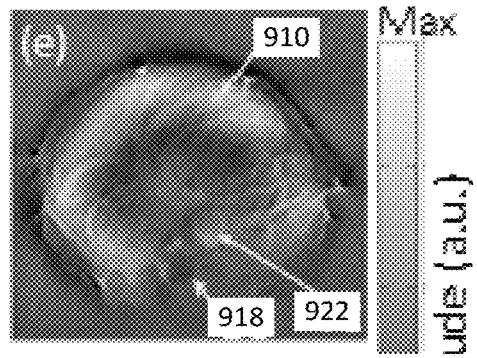
Figure 9B:
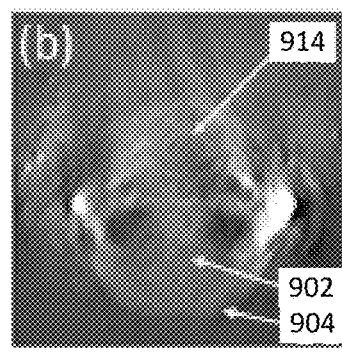

Athymic nude mice (5-6 weeks old) were imaged using the animal imaging system described herein above and illustrated in FIGS. 7A and 7B. FIGS. 9A, 9B, 9C, 9D, 9E, and 9F were acquired at 760 nm and formed purely based on the endogenous hemoglobin contrast. The half-time algorithm was utilized to reconstruct these images. FIG. 9A and FIG. 9B are cross-sectional view brain images acquired at different elevations. In FIG. 9A, the imaging plane was perpendicular to the skull. Due to the strong in-plane signal, the outer boundary of the brain was clearly visualized. As the imaging plane shifted out of a perpendicular orientation relative to the skull (FIG. 9B), the acoustic distortion from the skull became significant, blurring the outer boundary of the brain. In both FIG. 9A and FIG. 9B, the inner boundary of the brain was not clear, due to acoustic distortion from the nasal cavity. FIG. 9C is an in vivo cross-sectional image of the mouse heart. Because of the air cavities, the lung regions showed strong negative-amplitude signals and the heart region was blurry. Ghost objects were also observed close to the skin vessels, due to acoustic reflections from the lung. Image elements include 902: brain; 904: brain boundary; 906: heart; 908: lung; 910: left ventricle; 912: liver; 914: nasal cavity; 916: right ventricle; 918: spinal cord; 920: ghost objects; and 922: vena cave.

Figure 9D:
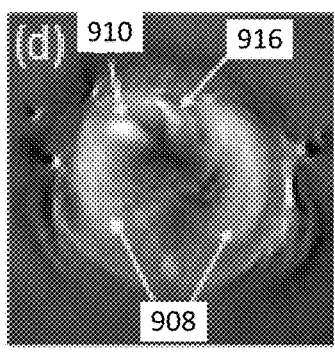

To demonstrate the feasibility of improving photoacoustic heart imaging using advanced image reconstruction algorithms, the mouse was euthanized and the lungs of the mouse were filled with water to remove the air cavities and to simulate the case when the acoustic distortion from the lung may be corrected using advanced image reconstruction algorithms. In FIG. 9D, the left and right ventricles of the heart may be clearly identified. The lungs also showed strong photoacoustic signals due to the dense pulmonary vessels. The mouse liver was also imaged and occupied almost the entire image cross section. Due to the absence of other organs and the use of the acoustic reflector, the image quality is enhanced relative to the brain and heart images. Detailed vascular structures within the liver were also visible, demonstrating that the system may be used for static and dynamic angiographic imaging.

Figure 9F:
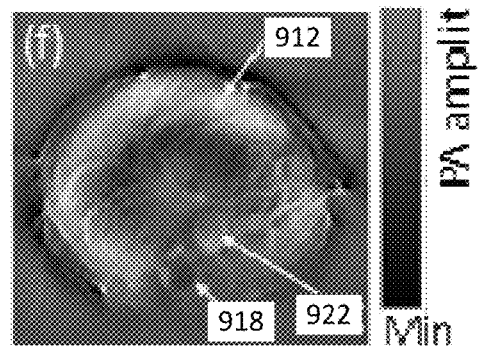

To demonstrate that 256 channels provided sufficient resolution for cross-sectional imaging, images were reconstructed using only those data associated with the 256 odd-numbered channels from the 512 channel data stream; the result is shown in FIG. 9F. Compared to the image (FIG. 9E) reconstructed from all 512 channels, the differences are negligible.

Figure 10A:
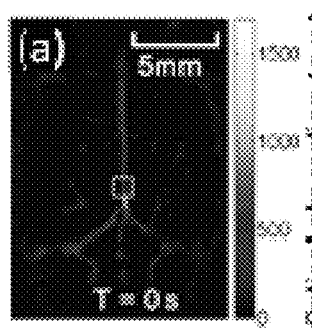
FIGS. 10A, 10B, 10C, and 10D are PA images of the wash-in process of Evans blue in cortical vasculature.
Figure 10B:
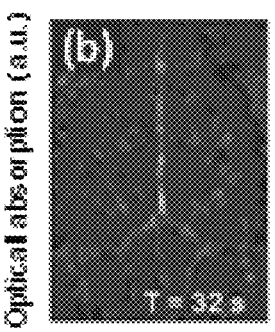
Figure 10C:
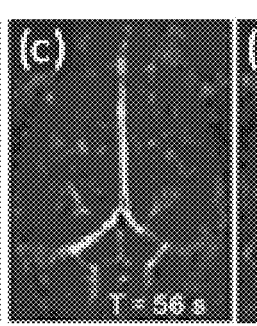
Figure 10D:
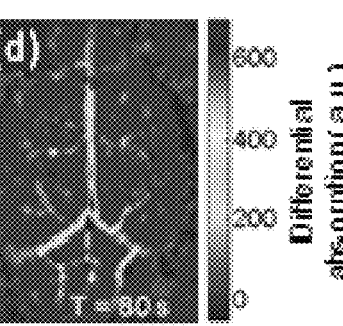

To demonstrate the feasibility of dynamic imaging, the wash-in process of a contrast dye in the mouse brain was imaged. After the control image was acquired (FIG. 10A), 0.1 ml Evans blue dye at 3% concentration was injected through the tail vein. The entire cortical region was then continuously imaged at 620 nm (the peak absorption wavelength for the dye) at a temporal resolution of 1.6 seconds/frame. FIGS. 10B, 10C, and 10D are graphs summarizing the differences between the pixel values of each image and the control image at three different post-injection times. Increases in the photoacoustic image values in both the hemispherical and the cerebellar vasculature may be clearly observed, demonstrating the increase in the dye concentration due to perfusion.

Example 7

Breast

Breast imaging using the system may use a half-ring or full-ring transducer array to detect acoustic signals including an unfocused 2.25 MHz (>80% bandwidth) 256-element full-ring transducer array (Imasonic Inc.) for a 2D full-view detection. A full-ring transducer array was 25 cm in diameter, providing adequate space for most breasts. The choice of transducer center frequency may tradeoff between resolution and penetration depth, taking into account one or more factors related to the characteristics of acoustic waveforms associated with breast tumors and/or the acoustic attenuation of breast tissue. The temporal profile of the pressure wave from a tumor with a given diameter is bipolar-shaped with a time duration of diameter/speed of sound (SOS). For small tumors with dimensions of the order of 0.7 mm, this time duration is about 0.47 µs, corresponding to a frequency of about 2.1 MHz, corresponding approximately to the transducer center frequency. With a center frequency of about 2.25 MHz, the transducer array may be capable of providing a resolution of about ~0.7 mm.

In addition, the acoustic attenuation from the center of the breast to the transducer array for a 7.5-cm radius breast is about 13 dB at 25 MHz given that the acoustic attenuation of the breast is 0.75 dB/(MHz·cm). Data processing methods include time-gain compensation and other image reconstruction algorithms discussed herein may mitigate the effect of acoustic attenuation.

Figure 11A:
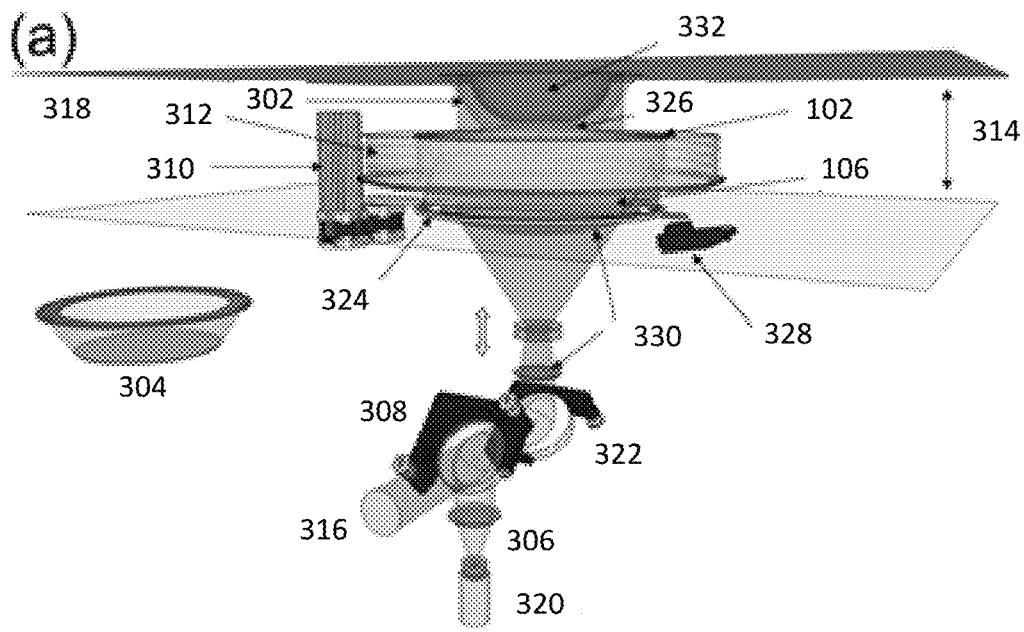
FIG. 11A is a perspective view of a PACT-USCT breast imaging system.
Figure 11B:
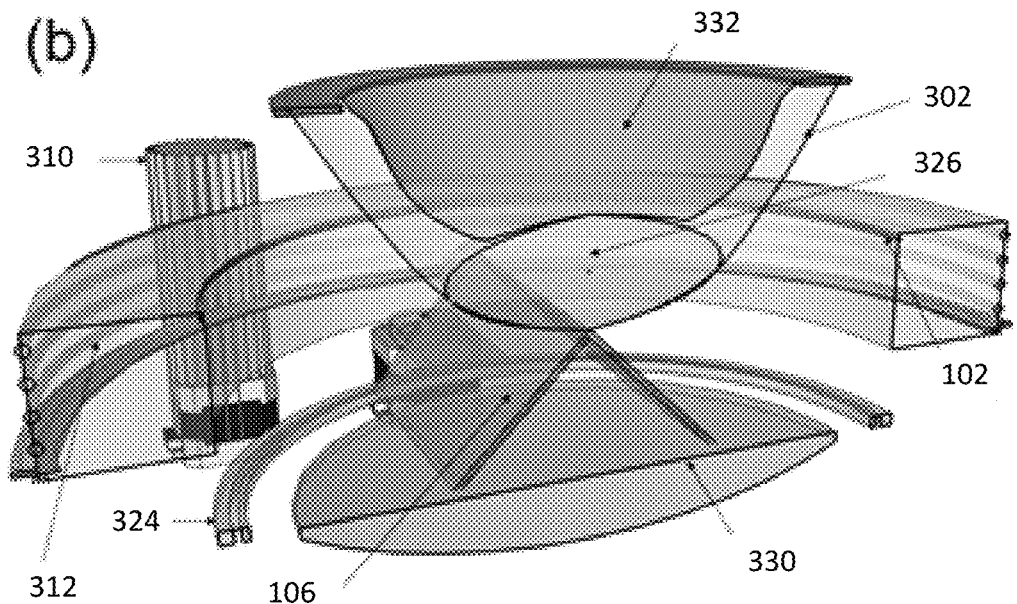
FIG. 11B is a cut-away view of the PACT-USCT breast imaging system.

FIG. 11A is a perspective view of a PACT-USCT breast imaging system. FIG. 11B is a cut-away view of the system, where 106 is the acoustic reflector (2 mirrors); 302 is the breast holder; 304 is the alternative breast holder with solid compression plate; 306 is the collimator; 308 is the dichroic mirror; 310 is the driving gear; 312 is the helical screw; 314 is the immersion tank; 316 is the laser beam; 318 is the patient bed; 320 is the pilot light source for alignment; 322 is the pointing mirror; 324 is the rotation table; 326 is the balloon spacer; 102 is the ring transducer array; 328 is the video camera for alignment and monitoring; 330 is the zoom lens assembly, and 332 is the breast.

The imaging system was mounted underneath a patient bed outfitted with a diameter opening attached to the breast holder (304). The breast holder was attached to the opening and may accommodate a breast of the patient lying prone on the patient bed. The breast may be slightly compressed against the chest wall by an ultrasonically and optically compatible breast holder with a balloon spacer (326). The custom-made breast holders have different diameters and thicknesses for different sizes of breasts. The breast holder was formed from polymethylpentene (TPX). The spacers may be formed from any suitable material including a thin low density polyethylene (LDPE) film filled with ultrasonic gel and a solid LDPE plate. Both the breast holder and spacer are optically transparent and have acoustic impedances close to that of breast tissue, thus having little influence on either light delivery or ultrasound propagation. A model of the breast holder and/or spacer was included in an imaging model to compensate for any confounding effects of these elements during image reconstruction. In addition, the nipple of the patient may be covered by a material such as gauze to reduce artifacts caused by high optical absorption of the tissues of the nipple.

The breast holder also isolates the patient from the imaging system for health and safety considerations. Local breast compression may also reduce the thickness of the breast in the light propagation direction, improve acoustic coupling, and reduce motion artifacts. Based on clinical experience with conventional breasts in the United States, the median depth of the locally compressed breast may be about 3-4 cm, well within the imaging depth capabilities of PACT (~6 cm). Deionized, degassed and sterile water was used to acoustically couple the breast to the holder, and silicone oil was used to couple the breast holder to the ultrasonic array (102), which was housed in an immersion tank (314). The immersion tank (314) was filled with a coupling medium including water or low-viscosity silicone oil, which has a 5 times smaller absorption coefficient than water for 1064-nm laser light, thereby reducing the attenuation of the laser fluence used during PACT during travel of the laser fluence through the immersion tank.

FIG. 12A shows a formation of virtual arrays by an acoustic reflector (106) in the system illustrated in FIGS. 11A and 11B, where 108 is the acoustic source; 402 is the direct beam; 404 is the reflected beam; 406 is the receiving element; 408 is the mirrored receiving element; 102 is the transducer array (ring); and 104 is the virtual array (2 half rings). FIG. 12B illustrates the spatial coverage by the transducer array 102 (cylinder) and the virtual array 104 (cap), where the inscribed spiral 410 is the trace of one element in the transducer array 102 and the virtual array 104 during mechanical scanning. FIG. 12C is an illustration of the spatial coverage with one half wavelength pitch by the aperture, where the disks 412 are TA elements.

During PACT imaging using the system the laser was adjusted by a zoom lens assembly 330 (in FIGS. 11A and 11B) to illuminate either the whole breast or be directed to a smaller region of interest. To increase the view aperture for 3D imaging, an acoustic reflector 106 was employed to form a virtual capped-cylindrical aperture. The acoustic reflector included two fused silica plates perpendicular to each other, and was oriented at an angle of 45 degrees relative to the Z-axis of the system. The distortion of the illumination light beam by the acoustic reflector may be negligible due to the similarity of the refractive index of the acoustic reflector and the surrounding water bath of the system. The ultrasonic waves, however, undergo multiple reflections with the fused silica acoustic reflectors if the incident angle of a photoacoustic wave is less than 24 degrees. However, this potentially confounding artifact is minimized because this range of incident angles is typically outside the viewing angle of the transducer elements. Therefore ultrasonic waves may be safely assumed to undergo total external reflection by the hard boundaries between the silica plates of the acoustic reflector and the surrounding water. As illustrated in FIG. 12A, an ultrasonic wave produced at any given point acoustic source (108) in the breast may be reflected by the acoustical reflector 106 to form a reflected beam (404). A receiving element on the array (406) may be mirror-projected onto a vertical plane, forming a virtual receiving element (408). As a result, the horizontal full-ring array may be mirror-imaged to form two vertically-oriented virtual overlapping half-ring arrays (104).

The method of 3D photoacoustic imaging with an acoustic reflector may be performed as follows. The acoustic reflector was removed from the field of view of the system by sliding it in a radial direction. The array was moved in the elevational (Z) direction to cover the whole compressed breast along a spiral trajectory; the array may move about 1.4 degrees in steps of about 0.14 degrees around the cylinder while moving along the cylinder in the Z direction with a step size of about 0.3 mm (FIG. 12B) by way of non-limiting example. The acoustic reflector (106) may be added and rotated over about 180 degrees around the Z-axis with an angle step of about 0.32 degrees. The transducer array may be rotated about 0.7 degrees, then the acoustic reflector may again rotate over about 180 degrees with an angle step of about 0.32 degree to finish a frame of 3D imaging.

The spiral scanning of the full-ring array may be similar to the spiral techniques widely used in X-ray CT scanners. The specified angle and step size enable the sampling pitch to be close to about ½ wavelength in both azimuthal and elevational directions to avoid generation of grating lobes. This scanning pattern may provide a cylindrical aperture for PACT and USCT applications. When the acoustic reflector rotates, the mirror image of each array element may rotate by the same angle around the Z-axis and may also move along the Z-axis, as shown by the spiral in FIG. 12B. Consequently, a virtual hemispherical array with about 1 mm spacing along the spiral and about 2 mm spacing between spirals may be formed. With an additional rotation of about 0.7 degrees of the transducer array, the position of the mirror image of each array element may shift a distance of about 1 mm.

The combination of the rotation of the acoustic reflector and the rotation of the transducer array may form a virtual hemispherical array with about 1 mm uniform pitch. The combination of all steps will provide a capped-cylindrical aperture with about 0.3 mm pitch in the cylinder and about 1 mm pitch in the cap for 3D PACT, providing a >2π sr solid angle. Such a large view aperture may enhance the image quality significantly, especially in the elevational direction; all boundaries may be reliably imaged. The frame rate may be determined from the rotational speed of the full-ring array and the reflector, the Z distance (≤about 6 cm) of the compressed breast, and the pulse repetition frequency of the laser (about 10 Hz) or ultrasound. For the proposed system, a 3D PACT scan may take about 10 min.

What is claimed is:

1. A photoacoustic imaging system comprising an ultrasound transducer array and a planar acoustic reflector positioned on an opposite side of a planar imaging region; wherein:

the planar acoustic reflector is configured to reflect one photoacoustic wave of a plurality of photoacoustic waves generated by a photoacoustic source within the planar imaging region to produce a reflected photoacoustic wave propagating toward the ultrasound transducer array, wherein the planar acoustic reflector includes two reflector planes intersecting each other at a non-zero angle; and the ultrasound transducer array is configured to receive another photoacoustic wave of the plurality of photoacoustic waves, the other photoacoustic wave propagating directly from the photoacoustic source, and is further configured to receive the reflected photoacoustic wave.

2. The system of claim 1, wherein the ultrasound transducer array is a full ring array.

3. The system of claim 2, wherein the ultrasound transducer array comprises one of a focused transducer array, an unfocused transducer array, and a transducer array comprising a combination of focused and unfocused transducers.

4. The system of claim 3, wherein the ultrasound transducer array is the focused transducer array.

5. The system of claim 4, further comprising an optics device configured to direct a light pulse suitable for photoacoustic imaging into the planar imaging region, wherein the optics device is chosen from:
 a. a diffuser configured to deliver a diffuse light pulse perpendicular to the planar imaging region; or
 b. a conical lens and a ring mirror configured to produce a planar light pulse within the planar imaging region.

6. The system of claim 3, wherein the ultrasound transducer array is the unfocused transducer array and the optics device is a conical lens and a ring mirror.

7. The system of claim 5, further comprising a translation stage operatively coupled to the ultrasound transducer array, the planar acoustic reflector, and the optics device, wherein the translation stage is configured to move the planar imaging region along an axis perpendicular to the planar imaging region.

8. The system of claim 1, wherein the planar acoustic reflector is operatively coupled to a motor configured to rotate the planar acoustic reflector about an axis perpendicular to the planar imaging region.

9. The system of claim 8, wherein the ultrasound transducer array is a full ring array operatively coupled to the motor, the motor further configured to rotate the ultrasound transducer array about an axis perpendicular to the planar imaging region.

10. The system of claim 1, wherein acoustic reflector is constructed from a material chosen from: boro silicate glass, sapphire, protected $MgF_2$ crystals, or fused silica plates.

11. The system of claim 2, wherein:
 a. the ultrasound transducer array is the full ring array
 b. the planar acoustic reflector further comprises an edge positioned along a diameter of the ultrasound transducer array; and
 c. the planar acoustic reflector is further positioned at a 45° angle relative to the planar imaging region.

12. A method of obtaining a photoacoustic image of a subject within a planar imaging region, the method comprising detecting a plurality of photoacoustic waves generated by at least one photoacoustic source within the planar imaging region using an ultrasound transducer array, the plurality of photoacoustic waves comprising:
 a. a direct photoacoustic wave propagating directly from one of the at least one photoacoustic sources to the ultrasound transducer array; and
 b. a reflected photoacoustic wave reflected to the ultrasound transducer array using a planar acoustic reflector positioned on a side of the planar imaging region opposite to the ultrasound transducer array, wherein the planar acoustic reflector includes two reflector planes intersecting each other at a non-zero angle.

13. The method of claim 12, further comprising recording a flight time for each of the plurality of photoacoustic waves, the flight time comprising a time elapsed between a delivery of a light pulse used to elicit the plurality of photoacoustic waves from within the planar imaging region and the detection of each of the plurality of photoacoustic waves.

14. The method of claim 13, further comprising locating each photoacoustic source by:
 a. estimating a distance between each of the at least one photoacoustic sources and each transducer in the ultrasound transducer array by dividing the flight time by a speed of sound within the planar imaging region for each photoacoustic wave detected by each transducer in the ultrasound transducer array;
 b. for each direct photoacoustic wave, locating a corresponding photoacoustic source along a detection axis of each transducer at the estimated distance; and
 c. for each reflected photoacoustic wave, locating the corresponding photoacoustic source at the estimated distance along a virtual detection axis of a virtual transducer in a virtual ultrasound transducer array, wherein the estimated distance is a summation of a first separation distance between the photoacoustic source and a location on the planar acoustic reflector and a second separation distance between the location and a corresponding transducer in the ultrasound transducer array corresponding to the virtual transducer.

15. The method of claim 14, wherein:
 a. the transducer array is a full ring array;
 b. the acoustic reflector further comprises an edge positioned along a diameter of the full ring array;
 c. the planar acoustic reflector is further positioned at a 45° angle relative to the planar imaging region; and
 d. the virtual array is a half-ring array positioned within a plane perpendicular to the planar imaging region and intersecting the planar imaging region at a diameter of the full ring array.

16. The method of claim 15, further comprising rotating the acoustic reflector about an array axis coincident with a centerline axis of the full ring array to obtain multiple photoacoustic images.

17. The method of claim 16, further comprising rotating the full ring array about the array axis.

18. The method of claim 14, further comprising translating the ultrasound transducer array and the acoustic mirror in a direction perpendicular to the planar imaging region to obtain photoacoustic images in at least two different planar imaging regions.

19. The method of claim 14, further comprising combining the photoacoustic images obtained in at least two different planar imaging regions to obtain a three-dimensional photoacoustic image of the subject.

* * * * *